(12) United States Patent
Matson et al.

(10) Patent No.: US 10,464,100 B2
(45) Date of Patent: Nov. 5, 2019

(54) SYSTEM AND PROCESS FOR FORMATION OF A TIME-RELEASED, DRUG-ELUTING TRANSFERABLE COATING

(75) Inventors: Dean W. Matson, Kennewick, WA (US); Clement R. Yonker, Sandpoint, ID (US); John L. Fulton, Richland, WA (US); George S. Deverman, Richland, WA (US); Barbara J. Tarasevich, Richland, WA (US); Wendy J. Shaw, Richland, WA (US); Leonard S. Fifield, Richland, WA (US); Krys Wallace, Richland, WA (US); C. Douglas Taylor, Franklinton, NC (US); James B. McClain, Raleigh, NC (US)

(73) Assignees: Micell Technologies, Inc., Durham, NC (US); Battelle Memorial Institute, Columbus, OH (US)

(*) Notice: Subject to any disclaimer, the term of this patent is extended or adjusted under 35 U.S.C. 154(b) by 574 days.

(21) Appl. No.: 14/122,862

(22) PCT Filed: May 30, 2012

(86) PCT No.: PCT/US2012/040040
§ 371 (c)(1),
(2), (4) Date: Aug. 11, 2014

(87) PCT Pub. No.: WO2012/166819
PCT Pub. Date: Dec. 6, 2012

(65) Prior Publication Data
US 2015/0024116 A1    Jan. 22, 2015

Related U.S. Application Data

(60) Provisional application No. 61/649,585, filed on May 21, 2012, provisional application No. 61/491,847, filed on May 31, 2011.

(51) Int. Cl.
*B05D 1/06* (2006.01)
*B05D 1/04* (2006.01)
(Continued)

(52) U.S. Cl.
CPC .............. *B05D 1/06* (2013.01); *A61L 29/085* (2013.01); *A61L 31/10* (2013.01); *B05D 1/04* (2013.01);
(Continued)

(58) Field of Classification Search
CPC .................................. A61F 2/00; B05D 1/04
(Continued)

(56) References Cited

U.S. PATENT DOCUMENTS 3,087,860 A    4/1963    Endicott
3,123,077 A    3/1964    Alcamo
(Continued)

FOREIGN PATENT DOCUMENTS

CA    2589761          12/2004
CA    2589761 A1        6/2006
(Continued)

OTHER PUBLICATIONS

Abreu Filho et al., "Influence of metal alloy and the profile of coronary stents in patients with multi-vessel coronary disease." Clinics 66(6):985-989 (2011).
(Continued)

*Primary Examiner* — Dah-Wei D. Yuan
*Assistant Examiner* — Andrew J Bowman
(74) *Attorney, Agent, or Firm* — Lerner, David, Littenberg, Krumholz & Mentlik, LLP

(57) ABSTRACT

A system and method are disclosed for coating surfaces of expandable medical devices with composite coatings. Coatings are composed of various materials including, e.g., polymers and drugs. Transfer of the coatings within a patient
(Continued)

or other host forms a drug-eluting coating that delivers time-released drugs over time for treatment of a medical condition.

43 Claims, 5 Drawing Sheets

(51) Int. Cl.
  *A61L 29/08* (2006.01)
  *A61L 31/10* (2006.01)
  *A61F 2/82* (2013.01)
  *A61K 9/70* (2006.01)
  *A61M 25/10* (2013.01)

(52) U.S. Cl.
  CPC ......... *A61F 2/82* (2013.01); *A61F 2250/0067* (2013.01); *A61K 9/7015* (2013.01); *A61M 2025/105* (2013.01); *A61M 2025/1031* (2013.01)

(58) Field of Classification Search
  USPC ................. 424/423; 427/2.24, 2.25, 475
  See application file for complete search history.

(56) References Cited

U.S. PATENT DOCUMENTS

| | | | |
|---|---|---|---|
| 3,457,280 | A | 7/1969 | Schmitt et al. |
| 3,597,449 | A | 8/1971 | Deprospero et al. |
| 3,929,992 | A | 12/1975 | Sehgal et al. |
| 4,000,137 | A | 12/1976 | Dvonch et al. |
| 4,285,987 | A | 8/1981 | Ayer et al. |
| 4,289,278 | A | 9/1981 | Itoh |
| 4,326,532 | A | 4/1982 | Hammar |
| 4,336,381 | A | 6/1982 | Nagata et al. |
| 4,582,731 | A | 4/1986 | Smith |
| 4,655,771 | A | 4/1987 | Wallsten |
| 4,733,665 | A | 3/1988 | Palmaz |
| 4,734,227 | A | 3/1988 | Smith |
| 4,734,451 | A | 3/1988 | Smith |
| 4,931,037 | A | 6/1990 | Wetterman |
| 4,950,239 | A | 8/1990 | Gahara |
| 4,985,625 | A | 1/1991 | Hurst |
| 5,000,519 | A | 3/1991 | Moore |
| 5,071,429 | A * | 12/1991 | Pinchuk ............... A61M 29/02 600/116 |
| 5,090,419 | A | 2/1992 | Palestrant |
| 5,096,848 | A | 3/1992 | Kawamura |
| 5,106,650 | A | 4/1992 | Hoy et al. |
| 5,158,986 | A | 10/1992 | Cha et al. |
| 5,195,969 | A | 3/1993 | Wang et al. |
| 5,243,023 | A | 9/1993 | Dezern |
| 5,270,086 | A | 12/1993 | Hamlin |
| 5,288,711 | A | 2/1994 | Mitchell et al. |
| 5,324,049 | A | 6/1994 | Mistrater et al. |
| 5,340,614 | A | 8/1994 | Perman et al. |
| 5,350,361 | A | 9/1994 | Tsukashima et al. |
| 5,350,627 | A | 9/1994 | Nemphos et al. |
| 5,342,621 | A | 10/1994 | Eury |
| 5,356,433 | A | 10/1994 | Rowland et al. |
| 5,366,504 | A | 11/1994 | Andersen et al. |
| 5,368,045 | A | 11/1994 | Clement et al. |
| 5,372,676 | A | 12/1994 | Lowe |
| 5,385,776 | A | 1/1995 | Maxfield et al. |
| 5,387,313 | A | 2/1995 | Thoms |
| 5,403,347 | A | 4/1995 | Roby et al. |
| 5,470,603 | A | 11/1995 | Staniforth et al. |
| 5,494,620 | A | 2/1996 | Liu et al. |
| 5,500,180 | A | 3/1996 | Anderson et al. |
| 5,556,383 | A | 9/1996 | Wang et al. |
| 5,562,922 | A | 10/1996 | Lambert |
| 5,569,463 | A | 10/1996 | Helmus et al. |
| 5,599,576 | A | 2/1997 | Opolski |
| 5,609,629 | A | 3/1997 | Fearnot et al. |
| 5,626,611 | A | 5/1997 | Liu et al. |
| 5,626,862 | A | 5/1997 | Brem et al. |
| 5,674,242 | A | 10/1997 | Phan et al. |
| 5,725,570 | A | 3/1998 | Heath |
| 5,800,511 | A | 9/1998 | Mayer |
| 5,811,032 | A | 9/1998 | Kawai et al. |
| 5,824,049 | A | 10/1998 | Ragheb et al. |
| 5,837,313 | A | 11/1998 | Ding et al. |
| 5,873,904 | A | 2/1999 | Ragheb et al. |
| 5,876,426 | A | 3/1999 | Kume et al. |
| 5,924,631 | A | 7/1999 | Rodrigues et al. |
| 5,948,020 | A | 9/1999 | Yoon et al. |
| 5,957,975 | A | 9/1999 | Lafont et al. |
| 5,980,972 | A * | 11/1999 | Ding .................. A61L 33/0011 427/2.24 |
| 6,013,855 | A | 1/2000 | McPherson et al. |
| 6,077,880 | A | 6/2000 | Castillo et al. |
| 6,129,755 | A | 10/2000 | Mathis et al. |
| 6,143,037 | A | 11/2000 | Goldsten et al. |
| 6,143,314 | A | 11/2000 | Chandrashekar et al. |
| 6,146,356 | A | 11/2000 | Wang et al. |
| 6,146,404 | A | 11/2000 | Kim et al. |
| 6,153,252 | A | 11/2000 | Hossainy et al. |
| 6,171,327 | B1 | 1/2001 | Daniel et al. |
| 6,190,699 | B1 | 2/2001 | Luzzi et al. |
| 6,206,914 | B1 | 3/2001 | Soykan et al. |
| 6,231,600 | B1 | 5/2001 | Zhong et al. |
| 6,245,104 | B1 | 6/2001 | Alt |
| 6,248,127 | B1 | 6/2001 | Shah et al. |
| 6,248,129 | B1 | 6/2001 | Froix |
| 6,273,913 | B1 | 8/2001 | Wright et al. |
| 6,280,802 | B1 | 8/2001 | Akedo et al. |
| 6,284,758 | B1 | 9/2001 | Egi et al. |
| 6,309,669 | B1 | 10/2001 | Setterstrom et al. |
| 6,319,541 | B1 | 11/2001 | Pletcher et al. |
| 6,336,934 | B1 | 1/2002 | Gilson et al. |
| 6,342,062 | B1 | 1/2002 | Suon et al. |
| 6,355,691 | B1 | 3/2002 | Goodman |
| 6,358,556 | B1 | 3/2002 | Ding et al. |
| 6,361,819 | B1 | 3/2002 | Tedeschi et al. |
| 6,364,903 | B2 | 4/2002 | Tseng et al. |
| 6,368,658 | B1 | 4/2002 | Schwartz et al. |
| 6,372,246 | B1 | 4/2002 | Wei et al. |
| 6,387,121 | B1 | 5/2002 | Alt |
| 6,409,716 | B1 | 6/2002 | Sahatjian et al. |
| 6,414,050 | B1 | 7/2002 | Howdle et al. |
| 6,416,779 | B1 | 7/2002 | D-Augustine et al. |
| 6,448,315 | B1 | 9/2002 | Lidgren et al. |
| 6,461,644 | B1 | 10/2002 | Jackson et al. |
| 6,495,163 | B1 | 12/2002 | Jordan |
| 6,497,729 | B1 | 12/2002 | Moussy et al. |
| 6,506,213 | B1 | 1/2003 | Mandel et al. |
| 6,517,860 | B1 | 2/2003 | Rosser et al. |
| 6,521,258 | B1 | 2/2003 | Mandel et al. |
| 6,524,698 | B1 | 2/2003 | Schmoock |
| 6,537,310 | B1 | 3/2003 | Palmaz et al. |
| 6,541,033 | B1 | 4/2003 | Shah |
| 6,572,813 | B1 | 6/2003 | Zhang et al. |
| 6,610,013 | B1 | 8/2003 | Fenster et al. |
| 6,627,246 | B2 | 9/2003 | Mehta et al. |
| 6,649,627 | B1 | 11/2003 | Cecchi et al. |
| 6,660,176 | B2 | 12/2003 | Tepper et al. |
| 6,669,785 | B2 | 12/2003 | DeYoung et al. |
| 6,669,980 | B2 | 12/2003 | Hanson et al. |
| 6,670,407 | B2 | 12/2003 | Howdle et al. |
| 6,682,757 | B1 | 1/2004 | Wright |
| 6,706,283 | B1 | 3/2004 | Appel et al. |
| 6,710,059 | B1 | 3/2004 | Labrie et al. |
| 6,720,003 | B2 | 4/2004 | Cheng et al. |
| 6,723,913 | B1 | 4/2004 | Barbetta |
| 6,726,712 | B1 | 4/2004 | Raeder-Devens et al. |
| 6,736,996 | B1 | 5/2004 | Carbonell et al. |
| 6,743,505 | B2 | 6/2004 | Antall et al. |
| 6,749,902 | B2 | 6/2004 | Yonker et al. |
| 6,755,871 | B2 | 6/2004 | Damaso et al. |
| 6,756,084 | B2 | 6/2004 | Fulton et al. |
| 6,767,558 | B2 | 7/2004 | Wang et al. |
| 6,780,475 | B2 | 8/2004 | Fulton et al. |
| 6,794,902 | B2 | 9/2004 | Becker et al. |

(56) References Cited

U.S. PATENT DOCUMENTS

| | | |
|---|---|---|
| 6,800,663 B2 | 10/2004 | Asgarzadeh et al. |
| 6,815,218 B1 | 11/2004 | Jacobsen et al. |
| 6,821,549 B2 | 11/2004 | Jayaraman |
| 6,837,611 B2 | 1/2005 | Kuo et al. |
| 6,838,089 B1 | 1/2005 | Carlsson et al. |
| 6,838,528 B2 | 1/2005 | Zhou |
| 6,858,598 B1 | 2/2005 | McKearn et al. |
| 6,860,123 B1 | 3/2005 | Uhlin et al. |
| 6,884,377 B1 | 4/2005 | Burnham et al. |
| 6,884,823 B1 | 4/2005 | Plerick et al. |
| 6,897,205 B2 | 5/2005 | Beckert et al. |
| 6,905,555 B2 | 6/2005 | DeYoung et al. |
| 6,908,624 B2 | 6/2005 | Hossainy et al. |
| 6,916,800 B2 | 7/2005 | McKearn et al. |
| 6,923,979 B2 | 8/2005 | Fotland et al. |
| 6,939,569 B1 | 9/2005 | Green et al. |
| 6,973,718 B2 | 12/2005 | Sheppard et al. |
| 7,148,201 B2 | 12/2006 | Stern et al. |
| 7,152,452 B2 | 12/2006 | Kokish |
| 7,160,592 B2 | 1/2007 | Rypacek et al. |
| 7,163,715 B1 | 1/2007 | Kramer |
| 7,169,404 B2 | 1/2007 | Hossainy et al. |
| 7,171,255 B2 | 1/2007 | Holupka et al. |
| 7,201,750 B1 | 4/2007 | Eggers et al. |
| 7,201,940 B1 | 4/2007 | Kramer |
| 7,229,837 B2 | 6/2007 | Chen |
| 7,279,174 B2 | 10/2007 | Pacetti et al. |
| 7,282,020 B2 | 10/2007 | Kaplan |
| 7,308,748 B2 | 12/2007 | Kokish |
| 7,326,734 B2 | 2/2008 | Zi et al. |
| 7,378,105 B2 | 5/2008 | Burke et al. |
| 7,419,696 B2 | 9/2008 | Berg et al. |
| 7,429,378 B2 | 9/2008 | Serhan et al. |
| 7,444,162 B2 | 10/2008 | Hassan |
| 7,455,688 B2 | 11/2008 | Furst et al. |
| 7,456,151 B2 | 11/2008 | Li et al. |
| 7,462,593 B2 | 12/2008 | Cuttitta et al. |
| 7,485,113 B2 | 2/2009 | Varner et al. |
| 7,488,389 B2 | 2/2009 | Osawa |
| 7,524,865 B2 | 4/2009 | D'Amato et al. |
| 7,537,610 B2 | 5/2009 | Reiss |
| 7,537,785 B2 | 5/2009 | Loscalzo et al. |
| 7,553,827 B2 | 6/2009 | Attawia et al. |
| 7,713,538 B2 | 5/2010 | Lewis et al. |
| 7,727,275 B2 | 6/2010 | Betts et al. |
| 7,763,277 B1 | 7/2010 | Canham et al. |
| 7,837,726 B2 | 11/2010 | Von Oepen et al. |
| 7,919,108 B2 | 4/2011 | Rees et al. |
| 7,955,383 B2 | 6/2011 | Krivoruchko et al. |
| 7,972,661 B2 | 7/2011 | Pui et al. |
| 8,097,292 B2 * | 1/2012 | Chen ................. B05B 5/08 427/2.24 |
| 8,298,565 B2 | 10/2012 | Taylor et al. |
| 8,758,429 B2 | 6/2014 | Taylor et al. |
| 8,795,762 B2 | 8/2014 | Fulton et al. |
| 8,834,913 B2 | 9/2014 | Shaw et al. |
| 2001/0026804 A1 | 10/2001 | Boutignon |
| 2001/0034336 A1 | 10/2001 | Shah et al. |
| 2001/0044629 A1 | 11/2001 | Stinson |
| 2001/0049551 A1 | 12/2001 | Tseng et al. |
| 2002/0007209 A1 | 1/2002 | Scheerder et al. |
| 2002/0051845 A1 | 5/2002 | Mehta et al. |
| 2002/0082680 A1 | 6/2002 | Shanley et al. |
| 2002/0091433 A1 | 7/2002 | Ding et al. |
| 2002/0099332 A1 | 7/2002 | Slepian et al. |
| 2002/0125860 A1 | 9/2002 | Schworm et al. |
| 2002/0133072 A1 | 9/2002 | Wang et al. |
| 2002/0144757 A1 | 10/2002 | Craig et al. |
| 2003/0001830 A1 | 1/2003 | Wampler et al. |
| 2003/0031699 A1 | 2/2003 | Van Antwerp |
| 2003/0077200 A1 | 4/2003 | Craig et al. |
| 2003/0088307 A1 | 5/2003 | Shulze et al. |
| 2003/0125800 A1 | 7/2003 | Shulze et al. |
| 2003/0143315 A1 | 7/2003 | Pui et al. |
| 2003/0170305 A1 | 9/2003 | O'Neil et al. |
| 2003/0180376 A1 | 9/2003 | Dalal et al. |
| 2003/0185964 A1 | 10/2003 | Weber et al. |
| 2003/0204238 A1 | 10/2003 | Tedeschi |
| 2003/0222017 A1 | 12/2003 | Fulton et al. |
| 2003/0222018 A1 | 12/2003 | Yonker et al. |
| 2003/0222019 A1 | 12/2003 | Fulton et al. |
| 2003/0232014 A1 | 12/2003 | Burke et al. |
| 2004/0013792 A1 | 1/2004 | Epstein et al. |
| 2004/0018228 A1 | 1/2004 | Fischell et al. |
| 2004/0022853 A1 | 2/2004 | Ashton et al. |
| 2004/0044397 A1 | 3/2004 | Stinson |
| 2004/0059290 A1 | 3/2004 | Palasis |
| 2004/0106982 A1 | 6/2004 | Jalisi |
| 2004/0122205 A1 | 6/2004 | Nathan |
| 2004/0126542 A1 | 7/2004 | Fujiwara et al. |
| 2004/0143317 A1 | 7/2004 | Stinson et al. |
| 2004/0157789 A1 | 8/2004 | Geall |
| 2004/0170685 A1 | 9/2004 | Carpenter et al. |
| 2004/0193177 A1 | 9/2004 | Houghton et al. |
| 2004/0193262 A1 | 9/2004 | Shadduck |
| 2004/0220660 A1 | 11/2004 | Shanley et al. |
| 2004/0224001 A1 | 11/2004 | Pacetti et al. |
| 2004/0236416 A1 | 11/2004 | Falotico |
| 2004/0260000 A1 | 12/2004 | Chaiko |
| 2005/0003074 A1 | 1/2005 | Brown et al. |
| 2005/0004661 A1 | 1/2005 | Lewis et al. |
| 2005/0010275 A1 | 1/2005 | Sahatjian et al. |
| 2005/0015046 A1 | 1/2005 | Weber et al. |
| 2005/0019747 A1 | 1/2005 | Anderson et al. |
| 2005/0038498 A1 | 2/2005 | Dubrow et al. |
| 2005/0048121 A1 | 3/2005 | East et al. |
| 2005/0049694 A1 | 3/2005 | Neary |
| 2005/0069630 A1 | 3/2005 | Fox et al. |
| 2005/0070990 A1 | 3/2005 | Stinson |
| 2005/0075714 A1 | 4/2005 | Cheng et al. |
| 2005/0079199 A1 | 4/2005 | Heruth et al. |
| 2005/0079274 A1 | 4/2005 | Palasis et al. |
| 2005/0084533 A1 | 4/2005 | Howdle et al. |
| 2005/0131513 A1 | 6/2005 | Myers |
| 2005/0147734 A1 | 7/2005 | Seppala et al. |
| 2005/0166841 A1 | 8/2005 | Robida |
| 2005/0175772 A1 | 8/2005 | Worsham et al. |
| 2005/0177223 A1 | 8/2005 | Palmaz |
| 2005/0191491 A1 | 9/2005 | Wang et al. |
| 2005/0196424 A1 | 9/2005 | Chappa |
| 2005/0208102 A1 | 9/2005 | Schultz |
| 2005/0216075 A1 | 9/2005 | Wang et al. |
| 2005/0238829 A1 | 10/2005 | Motherwell et al. |
| 2005/0255327 A1 | 11/2005 | Chaney et al. |
| 2005/0260186 A1 | 11/2005 | Bookbinder et al. |
| 2005/0268573 A1 | 12/2005 | Yan |
| 2005/0288481 A1 | 12/2005 | DesNoyer et al. |
| 2006/0001011 A1 | 1/2006 | Wilson et al. |
| 2006/0020325 A1 | 1/2006 | Burgermeister et al. |
| 2006/0030652 A1 | 2/2006 | Adams et al. |
| 2006/0045901 A1 | 3/2006 | Weber |
| 2006/0089705 A1 | 4/2006 | Ding et al. |
| 2006/0093771 A1 | 5/2006 | Rypacek et al. |
| 2006/0094744 A1 | 5/2006 | Maryanoff et al. |
| 2006/0116755 A1 | 6/2006 | Stinson |
| 2006/0121080 A1 | 6/2006 | Lye et al. |
| 2006/0121089 A1 | 6/2006 | Michal et al. |
| 2006/0134211 A1 | 6/2006 | Lien et al. |
| 2006/0136041 A1 | 6/2006 | Schmid et al. |
| 2006/0147698 A1 | 7/2006 | Carroll et al. |
| 2006/0153729 A1 | 7/2006 | Stinson et al. |
| 2006/0160455 A1 | 7/2006 | Sugyo et al. |
| 2006/0188547 A1 | 8/2006 | Bezwada |
| 2006/0193886 A1 | 8/2006 | Owens et al. |
| 2006/0193890 A1 | 8/2006 | Owens et al. |
| 2006/0198868 A1 | 9/2006 | DeWitt et al. |
| 2006/0210638 A1 | 9/2006 | Liversidge et al. |
| 2006/0216324 A1 | 9/2006 | Stucke et al. |
| 2006/0222756 A1 | 10/2006 | Davila et al. |
| 2006/0228415 A1 | 10/2006 | Oberegger et al. |
| 2006/0276877 A1 | 12/2006 | Owens et al. |
| 2007/0009564 A1 | 1/2007 | McClain et al. |
| 2007/0032864 A1 | 2/2007 | Furst et al. |
| 2007/0038227 A1 | 2/2007 | Massicotte et al. |

(56) References Cited

U.S. PATENT DOCUMENTS

| | | |
|---|---|---|
| 2007/0059350 A1 | 3/2007 | Kennedy et al. |
| 2007/0110888 A1 | 5/2007 | Radhakrishnan et al. |
| 2007/0123973 A1 | 5/2007 | Roth et al. |
| 2007/0123977 A1 | 5/2007 | Cottone et al. |
| 2007/0128274 A1 | 6/2007 | Zhu et al. |
| 2007/0148251 A1 | 6/2007 | Hossainy et al. |
| 2007/0154554 A1 | 7/2007 | Burgermeister et al. |
| 2007/0196423 A1 | 8/2007 | Ruane et al. |
| 2007/0198081 A1 | 8/2007 | Castro et al. |
| 2007/0203569 A1 | 8/2007 | Burgermeister et al. |
| 2007/0259017 A1 | 11/2007 | Francis |
| 2007/0280992 A1 | 12/2007 | Margaron et al. |
| 2008/0051866 A1 | 2/2008 | Chen et al. |
| 2008/0071359 A1 | 3/2008 | Thornton et al. |
| 2008/0075753 A1 | 3/2008 | Chappa |
| 2008/0077232 A1 | 3/2008 | Nishide |
| 2008/0095919 A1 | 4/2008 | McClain et al. |
| 2008/0097575 A1 | 4/2008 | Cottone |
| 2008/0097591 A1 | 4/2008 | Savage et al. |
| 2008/0107702 A1 | 5/2008 | Jennissen |
| 2008/0118543 A1 | 5/2008 | Pacetti et al. |
| 2008/0124372 A1 | 5/2008 | Hossainy et al. |
| 2008/0138375 A1 | 6/2008 | Yan et al. |
| 2008/0206304 A1 | 8/2008 | Lindquist et al. |
| 2008/0213464 A1 | 9/2008 | O'Connor |
| 2008/0255510 A1 | 10/2008 | Wang |
| 2008/0269449 A1 | 10/2008 | Chattopadhyay et al. |
| 2008/0292776 A1 | 11/2008 | Dias et al. |
| 2008/0300669 A1 | 12/2008 | Hossainy |
| 2008/0300689 A1 | 12/2008 | McKinnon et al. |
| 2009/0043379 A1 | 2/2009 | Prescott |
| 2009/0062909 A1 | 3/2009 | Taylor et al. |
| 2009/0068266 A1 | 3/2009 | Raheja et al. |
| 2009/0076446 A1 | 3/2009 | Dubuclet, IV et al. |
| 2009/0082855 A1 | 3/2009 | Borges et al. |
| 2009/0098178 A1 | 4/2009 | Hofmann et al. |
| 2009/0105809 A1 | 4/2009 | Lee et al. |
| 2009/0110711 A1 | 4/2009 | Trollsas et al. |
| 2009/0111787 A1 | 4/2009 | Lim et al. |
| 2009/0123515 A1* | 5/2009 | Taylor ............ A61L 31/10 424/423 |
| 2009/0186069 A1 | 7/2009 | DeYoung et al. |
| 2009/0202609 A1 | 8/2009 | Keough et al. |
| 2009/0216317 A1 | 8/2009 | Cromack et al. |
| 2009/0227949 A1 | 9/2009 | Knapp et al. |
| 2009/0231578 A1 | 9/2009 | Ling et al. |
| 2009/0263460 A1 | 10/2009 | McDonald |
| 2009/0285974 A1 | 11/2009 | Kerrigan et al. |
| 2009/0292351 A1 | 11/2009 | McClain et al. |
| 2009/0292776 A1 | 11/2009 | Nesbitt et al. |
| 2009/0297578 A1 | 12/2009 | Trollsas et al. |
| 2009/0300689 A1 | 12/2009 | Conte et al. |
| 2010/0015200 A1 | 1/2010 | McClain et al. |
| 2010/0030261 A1 | 2/2010 | McClain |
| 2010/0042206 A1 | 2/2010 | Yadav et al. |
| 2010/0055145 A1 | 3/2010 | Betts et al. |
| 2010/0055294 A1 | 3/2010 | Wang et al. |
| 2010/0063570 A1 | 3/2010 | Pacetti et al. |
| 2010/0063580 A1 | 3/2010 | McClain et al. |
| 2010/0074934 A1 | 3/2010 | Hunter |
| 2010/0155496 A1 | 6/2010 | Stark et al. |
| 2010/0166869 A1 | 7/2010 | Desai et al. |
| 2010/0196482 A1 | 8/2010 | Radovic-Moreno et al. |
| 2010/0198330 A1 | 8/2010 | Hossainy et al. |
| 2010/0198331 A1 | 8/2010 | Rapoza et al. |
| 2010/0211164 A1 | 8/2010 | McClain et al. |
| 2010/0228348 A1 | 9/2010 | McClain et al. |
| 2010/0233332 A1 | 9/2010 | Xing et al. |
| 2010/0239635 A1 | 9/2010 | McClain et al. |
| 2010/0241220 A1 | 9/2010 | McClain et al. |
| 2010/0256746 A1 | 10/2010 | Taylor et al. |
| 2010/0256748 A1 | 10/2010 | Taylor et al. |
| 2010/0272778 A1 | 10/2010 | McClain et al. |
| 2010/0298928 A1 | 11/2010 | McClain et al. |
| 2011/0009953 A1 | 1/2011 | Luk et al. |
| 2011/0034422 A1 | 2/2011 | Kannan et al. |
| 2011/0159069 A1 | 6/2011 | Shaw et al. |
| 2011/0160751 A1 | 6/2011 | Granja Filho |
| 2011/0190864 A1 | 8/2011 | McClain et al. |
| 2011/0238161 A1 | 9/2011 | Fulton et al. |
| 2011/0257732 A1 | 10/2011 | McClain et al. |
| 2011/0264190 A1 | 10/2011 | McClain et al. |
| 2011/0301697 A1 | 12/2011 | Hoffmann et al. |
| 2012/0064124 A1 | 3/2012 | McClain et al. |
| 2012/0064143 A1 | 3/2012 | Sharp et al. |
| 2012/0065723 A1 | 3/2012 | Drasler et al. |
| 2012/0101566 A1 | 4/2012 | Mews et al. |
| 2012/0150275 A1 | 6/2012 | Shaw-Klein |
| 2012/0172787 A1 | 7/2012 | McClain et al. |
| 2012/0177742 A1 | 7/2012 | McClain et al. |
| 2012/0271396 A1 | 10/2012 | Zheng et al. |
| 2012/0280432 A1 | 11/2012 | Chen et al. |
| 2012/0323311 A1 | 12/2012 | McClain et al. |
| 2013/0006351 A1 | 1/2013 | Taylor et al. |
| 2013/0172853 A1 | 7/2013 | McClain et al. |

FOREIGN PATENT DOCUMENTS

| | | |
|---|---|---|
| CN | 1465410 | 1/2004 |
| CN | 1465410 A | 1/2004 |
| CN | 1649551 | 8/2005 |
| EP | 0604022 | 6/1994 |
| EP | 0982041 | 3/2000 |
| EP | 1195822 A2 | 4/2002 |
| EP | 1454677 | 9/2004 |
| EP | 2197070 A1 | 6/2010 |
| EP | 2293357 A1 | 3/2011 |
| EP | 2293366 A1 | 3/2011 |
| JP | 1994-098902 | 4/1994 |
| JP | H09-056807 | 3/1997 |
| JP | 2003-205037 | 7/2003 |
| JP | 2003-533286 | 11/2003 |
| JP | 2003-533493 | 11/2003 |
| JP | 2003533492 | 11/2003 |
| JP | 2004/173770 | 6/2004 |
| JP | 2004-518458 | 6/2004 |
| JP | 2004-529674 | 9/2004 |
| JP | 2005-505318 | 2/2005 |
| JP | 2005-523119 | 8/2005 |
| JP | 2005-523332 | 8/2005 |
| JP | 2005-296690 | 10/2005 |
| JP | 2009-501566 | 1/2009 |
| KR | 10-2004-0034064 | 4/2004 |
| WO | WO-95/006487 | 3/1995 |
| WO | WO-96/20698 | 7/1996 |
| WO | WO-97/045502 | 12/1997 |
| WO | WO-2001/054662 | 8/2001 |
| WO | WO-2001-087371 | 11/2001 |
| WO | WO-2001/087372 | 11/2001 |
| WO | WO-2002/040702 | 5/2002 |
| WO | WO 2002/043799 | 6/2002 |
| WO | WO-2002-074194 A2 | 9/2002 |
| WO | WO-2002/090085 | 11/2002 |
| WO | WO-2003/039553 | 5/2003 |
| WO | WO-2003-082368 A | 10/2003 |
| WO | WO-2003/101624 A1 | 12/2003 |
| WO | WO-2004/009145 | 1/2004 |
| WO | WO-2004/028589 | 4/2004 |
| WO | WO-2004/043506 | 5/2004 |
| WO | WO-2004/045450 | 6/2004 |
| WO | WO-2004/098574 | 11/2004 |
| WO | WO-2005/042623 A1 | 5/2005 |
| WO | WO-2005/063319 | 7/2005 |
| WO | WO-2005/069889 | 8/2005 |
| WO | WO-2005/117942 A2 | 12/2005 |
| WO | WO-2006/014534 | 2/2006 |
| WO | WO-2006/052575 | 5/2006 |
| WO | WO-2006/065685 | 6/2006 |
| WO | WO-2006/083796 A2 | 8/2006 |
| WO | WO-2006/099276 A2 | 9/2006 |
| WO | WO-2007-002238 | 1/2007 |
| WO | WO-2007/011707 A2 | 1/2007 |
| WO | WO-2007/011708 A2 | 1/2007 |
| WO | WO-2007/092179 | 8/2007 |

(56) References Cited

FOREIGN PATENT DOCUMENTS

| | | |
|---|---|---|
| WO | WO-2007/127363 A2 | 11/2007 |
| WO | WO 2007/143609 | 12/2007 |
| WO | WO-2008/042909 | 4/2008 |
| WO | WO-2008/046641 | 4/2008 |
| WO | WO-2008/046642 | 4/2008 |
| WO | WO-2008/052000 | 5/2008 |
| WO | WO-2008/070996 | 6/2008 |
| WO | WO-2008/086369 | 7/2008 |
| WO | WO 2008/131131 A1 | 10/2008 |
| WO | WO-2008/0148013 | 12/2008 |
| WO | WO-2009/051780 | 4/2009 |
| WO | WO-2009/0146209 | 12/2009 |
| WO | WO-2010/009335 | 1/2010 |
| WO | WO-2010/075590 | 7/2010 |
| WO | WO-2010/111196 A2 | 9/2010 |
| WO | WO-2010/111196 A3 | 9/2010 |
| WO | WO-2010/111232 A3 | 9/2010 |
| WO | WO-2010/111232 A9 | 9/2010 |
| WO | WO-2010/111238 A2 | 9/2010 |
| WO | WO-2010/111238 A3 | 9/2010 |
| WO | WO-2010/120552 A2 | 10/2010 |
| WO | WO-2010/120552 A3 | 10/2010 |
| WO | WO-2010/121187 A2 | 10/2010 |
| WO | WO-2010/121187 A3 | 10/2010 |
| WO | WO-2011/009096 A1 | 1/2011 |
| WO | WO-2011/097103 | 8/2011 |
| WO | WO-2011/119762 | 9/2011 |
| WO | WO-2011/130448 | 10/2011 |
| WO | WO-2011/133655 | 10/2011 |
| WO | WO-2012/009684 | 1/2012 |
| WO | WO-2012/034079 | 3/2012 |
| WO | WO-2012/082502 | 6/2012 |
| WO | WO-2012/092504 | 7/2012 |
| WO | WO-2012/142319 | 10/2012 |
| WO | WO-2012/166819 | 12/2012 |
| WO | WO-2013/012689 | 1/2013 |
| WO | WO-2013/025535 | 2/2013 |
| WO | WO-2013/059509 | 4/2013 |
| WO | WO-2013/173657 | 11/2013 |
| WO | WO-2013/177211 | 11/2013 |
| WO | WO-2014/063111 | 4/2014 |

OTHER PUBLICATIONS

Akoh et al., "One-Stage Synthesis of Raffinose Fatty Acid Polyesters." Journal Food Science 52:1570 (1987).
Albert et al., "Antibiotics for preventing recurrent urinary tract infection in non-pregnant women." Cochrane Database System Rev. 3, CD001209 (2004).
Au et al., "Methods to improve efficacy of intravesical mitomycin C: Results of a randomized phase III trial." Journal of the National Cancer Institute, 93(8), 597-604 (2001).
AU2006270221 Exam Report dated Apr. 6, 2010.
AU2007243268 Exam Report dated May 15, 2013.
AU2007243268 Exam Report dated Aug. 31, 2011.
AU2009251504 Exam Report dated Dec. 8, 2011.
AU2009270849 Exam Report dated Feb. 14, 2012.
AU2011232760 Exam Report dated Apr. 10, 2013.
AU2011256902 Exam Report dated Jun. 13, 2013.
AU2012203203 Exam Report dated Apr. 12, 2013.
AU2012203577 Exam Report dated Jun. 7, 2013.
AU2011256902 Exam Report dated Jun. 10, 2014.
Balss et al., "Quantitative spatial distribution of sirolumus and polymers in drug-eluting stents using confocal Raman microscopy." J. of Biomedical Materials Research Part A, 258-270 (2007).
Belu et al., "Three-Dimensional Compositional Analysis of Drug Eluting Stent Coatings Using Cluster Secondary Loan Mass Spectroscopy." Anal. Chem. 80:624-632 (2008).
Belu, et al., "Chemical imaging of drug eluting coatings: Combining surface analysis and confocal Rama microscopy." J. Controlled Release 126: 111-121 (2008).
Boneff, "Topical Treatment of Chronic Prostatitis and Premature Ejaculation," International Urology and Nephrology 4(2):183-186 (1971).
Bookbinder et al., "A recombinant human enzyme for enhanced interstitial transport of therapeutics." Journal of Controlled Release 114:230-241 (2006).
Borchert et al., "Prevention and treatement of urinary tract infection with probiotics: Review and research perspective," Indian Journal Urol. 24(2):139-144 (2008).
Brunstein et al., "Histamine, a vasoactive agent with vascular disrupting potential improves tumour response by enhancing local drug delivery," British Journal of Cancer 95:1663-1669 (2006).
Bugay et al., "Raman Analysis of Pharmaceuticals," in "Applications of Vibrational Spectroscopy in Pharmaceutical Research and Development," Ed. Pivonka, D.E., Chalmers, J.M., Griffiths, P.R. Wiley and Sons, p. 1-24. (2007).
CA 2757276 Office Action dated Feb. 15, 2013.
CA 2757276 Office Action dated Feb. 5, 2014.
CA 2794704 Office Action dated Feb. 7, 2014.
CA 2613280 Office Action dated Oct. 2, 2012.
CA 2615452 Office Action dated Dec. 19, 2012.
CA 2615452 Office Action dated Oct. 8, 2013.
CA 2650590 Office Action dated Jul. 23, 2013.
CA 2613280 Office Action dated Dec. 10, 2013.
CA 2667228 Office Action dated Jan. 22, 2014.
CA 2679712 Office Action dated Feb. 24, 2014.
CA 2684482 Office Action dated Nov. 10, 2011.
CA 2684482 Office Action dated Jul. 11, 2012.
CA 2688314 Office Action dated Jun. 6, 2012.
CA 2667228 Office Action dated May 7, 2013.
CA 2730995 Office Action dated May 29, 2013.
CA 2730995 Office Action dated Sep. 26, 2012.
CA 2730995 Office Action dated Feb. 20, 2014.
CA 2756307 Office Action dated Feb. 18, 2013.
CA 2756307 Office Action dated Mar. 24, 2014.
CA 2756386 Office Action dated Mar. 15, 2013.
CA 2756388 Office Action dated Apr. 11, 2013.
CA 2756388 Office Action dated Apr. 14, 2014.
CA 2759015 Office Action dated Apr. 8, 2013.
CA 2759015 Office Action dated Jul. 21, 2014.
CA 2756386 Office Action dated Oct. 24, 2013.
CA 2756386 Office Action dated May 16, 2014.
CA 2805631 Office Action dated Jan. 17, 2014.
CA 2823355 Office action dated Apr. 14, 2014.
Cadieux et al., "Use of triclosan-eluting ureteral stents in patients with long-term stents." J. Endourol (Epub) (Jun. 19, 2009).
Channon et al., "Nitric Oxide Synthase in Atherosclerosis and Vascular Injury: Insights from Experimental Gene Therapy." Arteriosclerosis, Thrombosis and Vascular Biology, 20(8):1873-1881 (2000).
Chen et al. Immobilization of heparin on a silicone surface through a heterobifunctional PEG spacer. Biomaterials. 26(35):7418-24 (2005).
Cholpek et al. "The influence of carbon fibres on the resorption time and mechanical properties of the lactide-glycolide co-polymer." J. Biomater. Sci. Polymer Edn, vol. 18, No. 11, pp. 1355-1368 (2007).
Clair and Burks, "Thermoplastic/Melt-Processable Polyimides," NASA Conf. Pub. #2334, pp. 337-355 (1984).
CN 2006800258093 Office Action dated May 30, 2012.
CN 200780047425.6 Office Action dated Aug. 3, 2012.
CN 200780047425.6 Office Action dated Feb. 28, 2013.
CN 200880007308.1 Office Action dated Jul. 3, 2013.
CN 200880007308.1 Office Action dated Nov. 23, 2011.
CN 200880007308.1 Office Action dated Oct. 18, 2012.
CN 200880007308.1 Office Action dated Jan. 2, 2014.
CN 200880020515 Office Action dated Jul. 22, 2013.
CN 200880020515 Office Action dated Oct. 9, 2012.
CN 200880020515 Office Action dated Apr. 15, 2014.
CN 200880100102.3 Office Action dated Apr. 11, 2013.
CN 200880100102.3 Office Action dated Jun. 1, 2012.
CN 200880100102.3 Office Action dated Dec. 11, 2013.
CN 200880100102.3 Office Action dated Aug. 27, 2014.
CN 200980122691 Office Action dated Oct. 10, 2012.
CN 200980136432.2 Office Action dated Jan. 14, 2013.

(56) References Cited

OTHER PUBLICATIONS

CN 200980136432.2 Office Action dated Nov. 4, 2013.
CN 200980136432.2 Office Action dated Jul. 3, 2014.
CN 201080024973.9 Office Action dated Dec. 20, 2013.
CN 201080024973.9 Office Action dated Aug. 7, 2014.
Cohen, et al. "Sintering Technique for the Preparation of Polymer Matrices for the Controlled Release of Macromolecules." Journal of Pharmaceutical Sciences, 73:8, 1034-1037 (1984).
Colombo et al. "Selection of Coronary Stents." Journal of the American College of Cardiology, vol. 40, No. 6, p. 1021-1033 (2002).
CRC Handbook of chemistry and physics. 71st ed. David R. Lide, Editor-in-Chief. Boca Raton, FL, CRC Press; 1990; 6-140.
Cyrus et al., "Intramural delivery of rapamycin with alphavbeta3-targeted paramagnetic nanoparticles inhibits stenosis after balloon injury." Arterioscler Thromb Vasc Biol 28:820-826 (2008).
Derwent-ACC-NO: 2004-108578 Abstracting 2004003077; Jan. 8, 2004; 3 pages.
DiSTASI et al., "Percutaneous sequential bacillus Calmette-Guerin and mitomycin C for panurothelial carcinomatosis," Can. J. Urol. 12(6):2895-2898 (2005).
Domb and Langer, "Polyanhydrides. I. Preparation of High Molecular Weight Polyanhydrides. "J. Polym Sci. 25:3373-3386 (1987).
Domingo, C. et al., "Precipication of ultrafine organic crystals from the rapid expansion of supercritical solutions over a capillary and a frit nozzle." J. Supercritical Fluids 10:39-55 (1997).
Dzik-Jurasz, "Molecular imaging in vivo: an introduction." The British Journal of Radiology, 76:S98-S109 (2003).
EA 200901254 Office Action dated Jul. 29, 2013.
EA 200901254/28 Office Action dated Jun. 28, 2012.
EA 201001497 Office Action dated Feb. 13, 2013.
EA 201001497 Office Action dated Jul. 29, 2013.
Electrostatic Process, Wiley Encyclopedia of Electrical and Electronics Engineering, John Wiley & Sons, Inc. 1999; 7:15-39.
Eltze et al., "Imidazoquinolinon, imidazopyridine, and isoquinolindione derivatives as novel and potent inhibitors of the poly (ADP-ribose) polymerase (PARP): a comparison with standard PARP inhibitors," Mol. Pharmacol 74(6):1587-1598 (2008).
EP06773731.2 Search Report dated Oct. 2, 2012.
EP06787258.0 Office Action dated Mar. 15, 2013.
EP06787258.0 Search Report dated Feb. 6, 2012.
EP07756094.4 Office Action dated Jan. 21, 2014.
EP07756094.4 Office Action dated May 29, 2013.
EP07756094.4 Search Report dated Aug. 31, 2012.
EP08705772.5 Office Action dated Oct. 30, 2013.
EP08705772.5 Search Report dated Feb. 20, 2013.
EP08733210.2 Office Action dated Jul. 16, 2013.
EP08733210.2 Search Report dated Oct. 23, 2012.
EP08756215.3 Search Report dated Oct. 5, 2011.
EP08756215.3 Search Report dated Jan. 28, 2013.
EP09755571.8 Office Action dated Dec. 13, 2013.
EP09755571.8 Search Report dated Apr. 9, 2013.
EP09798764.8 Search Report dated Sep. 30, 2013.
EP09805981.9 Office Action dated Feb. 13, 2013.
EP10756676.2 Search Report dated Jan. 31, 2014.
EP10756696.0 Search Report dated Oct. 10, 2013.
EP10764884.2 Search Report dated Oct. 28, 2013.
EP10765295.0 Search Report dated Oct. 17, 2013.
EP11769546.0 Search Report dated Sep. 19, 2013.
EP10800642.0 Search Report dated Mar. 19, 2014.
EP11772624.0 Search Report dated Jun. 5, 2014.
EP09798764.8 Office Action dated Jun. 30, 2014.
Ettmayer et al. Lessons learned from marketed and investigational prodrugs. J Med Chem. 47(10):2393-404 (2004).
Fibbi et al., "Chronic inflammation in the pathogenesis of benign prostatic hyperplasia." Int J Androl. 33(3):475-88 (2010).
Fleischmann et al., "High Expression of Gastrin-Releasing Peptide Receptors in the Vascular bed of Urinary Tract Cancers: Promising Candidates for Vascular Targeting Applications." Endocr. Relat. Cancer 16(2):623-33 (2009).

Froehlich et al., "Conscious sedation for gastroscopy: patient tolerance and cardiorespiratory parameters," Gastroenterology 108(3):697-704 (1995).
Fujiwara et al., "Insulin-like growth factor 1 treatment via hydrogels rescues cochlear hair cells from ischemic injury." NeuroReport 19(16):1585-1588 (2008).
Fulton et al. Thin Fluoropolymer films and nanoparticle coatings from the rapid expansion of supercritical carbon dioxide solutions with electrostatic collection, Polymer Communication. 2627-3632 (2003).
Green et al., "Simple conjugated polymer nanoparticles as biological labels," Proc Roy Soc A. published online Jun. 24, 2009 doi:10.1098/rspa.2009.0181.
Griebenow et al., "On Protein Denaturation in Aqueous-Organic Mixtures but not in Pure Organic Solvents," J. Am Chem Soc., vol. 118. No. 47, 11695-11700 (1996).
Hamilos et al., "Differential effects of Drug-Eluting Stents on Local Endothelium-Dependent Coronary Vasomotion." JACC vol. 51, No. 22, Endothelium and DES, 2123-9 (2008).
Han, et al., "Studies of a Novel Human Thrombomodulin Immobilized Substrate: Surface Characterization and Anticoagulation Activity Evaluation." J. Biomater. Sci. Polymer Edn, 12 (10):1075-1089 (2001).
Hartmann et al., "Tubo-ovarian abscess in virginal adolescents: exposure of the underlying etiology," J. Pediatr Adolesc Gynecol, 22(3):313-16 (2009).
Hasegawa et al., "Nylong 6/Na-montmorillonite nanocomposites prepared by compounding Nylon 6 with Na-montmorillonite slurry," Polymer 44:2933-2937 (2003).
Hinds, WC. Aerosol Technology, Properties, Behavior and Measurement of Airborne Particles, Department of Environmental Health Sciences, Harvard University School of Public Health, Boston, Massachusetts. 1982; 283-314.
Hladik et al., "Can a topical microbicide prevent rectal HIV transmission?" PLoS Med. 5(8):e167 (2008).
Iconomidou et al., "Secondary Structure of Chorion Proteins of the Teleosatan Fish Dentex dentex by ATR FR-IR and FT-Raman Spectroscopy," J. of Structural Biology, 132, 112-122 (2000).
ID—W00201003529 Office Action dated Apr. 28, 2014.
IL—208648 Official Notification dated Feb. 9, 2012.
IL—201550 Official Notification dated Dec. 8, 2013.
IN-368/DELNP/2008 Exam Report dated Oct. 17, 2011.
IN-6884/DELNP/2009 Office Action dated Oct. 31, 2013.
IN-7740/DELNP/2009 Office Action dated Jul. 29, 2014.
Jackson et al., "Characterization of perivascular poly(lactic-co-glycolic acid) films containing paclitaxel" *Int. J. of Pharmaceutics*, 283:97-109 (2004).
Jensen et al., Neointimal hyperplasia after sirollmus-eluting and paclitaxel-eluting stend implantation in diabetic patients: the randomized diabetes and drug eluting stent (DiabeDES) intravascular ultrasound trial. European heart journal (29), pp. 2733-2741. Oct. 2, 2008. Retrieved from the Internet. Retrieved on [Jul. 17, 2012]. URL:<http://eurheartj.oxfordjournals.org/content/29/22/2733.full.pdf> entire document.
Jewell, et al., "Release of Plasmid DNA from Intravascular Stents Coated with Ultrathin Multilayered Polyelectrolyte Films" Biomacromolecules. 7: 2483-2491 (2006).
Johns, H.E, J.R.Cunningham, Thomas, Charles C., Publisher, "The Physics of Radiology, " Springfield, IL, pp. 133-143 (1983).
Joner et al. "Site-specific targeting of nanoparticle prednisolone reduces in-stent restenosis in a rabbit model of established atheroma," Arterioscler Thromb Vasc Biol. 28:1960-1966 (2008).
Jovanovic et al. "Stabilization of Proteins in Dry Powder Formulations Using Supercritical Fluid Technology," Pharm. Res. 21(11), (2004).
JP 2008-521633 Office Action dated Oct. 12, 2012.
JP2008-521633 Office Action dated Dec. 28, 2011.
JP-2009-534823 Office Action dated Apr. 23, 2013.
JP-2009-534823 Office Action dated Feb. 21, 2012.
JP-2009-534823 Office Action dated Sep. 20, 2012.
JP-2009-545647 Office Action dated Jun. 5, 2012.
JP-2009-545647 Office Action dated May 14, 2013.
JP-2009-545647 Office Action dated Apr. 22, 2014.

(56) References Cited

OTHER PUBLICATIONS

JP-2010-504253 Office Action dated Dec. 12, 2011.
JP-2010-504253 Office Action dated Dec. 7, 2012.
JP-2010-510441 Office Action dated May 7, 2013.
JP-2011-505248 Office Action dated Jun. 4, 2013.
JP-2011-518920 Office Action dated Dec. 17, 2012.
JP-2011-518920 Office Action dated Oct. 23, 2013.
JP-2012-503677 Office Action dated Jan. 18, 2013.
JP-2012-503677 Office Action dated Nov. 1, 2013.
JP-2012-151964 Office Action dated Dec. 10, 2013.
JP-2013-024508 Office Action dated May 2, 2014.
JP-2013-190903 Office Action dated Sep. 2, 2014.
Kazemi et al., "The effect of betamethasone gel in reducing sore throat, cough, and hoarseness after laryngo-tracheal intubation," Middle East J. Anesthesiol. 19(1):197-204 (2007).
Kehinde et al., "Bacteriology of urinary tract infection associated with indwelling J ureteral stents," J. Endourol. 18(9):891-896 (2004).
Kelly et al., "Double-balloon trapping technique for embolization of a large wide-necked superior cerebellar artery aneurysm: case report," Neurosurgery 63(4 Suppl 2):291-292 (2008).
Khan et al., "Chemistry and the new uses of Sucrose: How Important?" Pur and Appl. Chem 56:833-844 (1984).
Khan et al., "Cyclic Acetals of 4,1',6'-Trichloro-4,1',6',-Trideoxy-Trideoxy-galacto-Sucrose and their Conversion into Methyl Ether Derivatives." Carb. Res. 198:275-283 (1990).
Khan et al., "Enzymatic Regioselective Hydrolysis of Peracetylated Reducing Disaccharides, Specifically at the Anomeric Centre: Intermediates for the Synthesis of Oligosaccharides." Tetrahedron Letters 34:7767 (1933).
Khayankarn et al., "Adhesion and Permeability of Polyimide-Clay Nanocomposite Films for Protective Coatings," Journal of Applied Polymer Science, vol. 89, 2875-2881 (2003).
Koh et al., A novel nanostructured poly(lactic-co-glycolic-acid)—multi-walled carbon nanotube composite for blood-contacting applications: Thrombogenicity studies, Acta Biomaterialia 5:3411-3422 (2009).
KR10-2008-7003756 Office Action dated Sep. 23, 2013.
KR10-2008-7003756 Office Action dated Oct. 30, 2012.
KR 10-2013-7031237 Office Action dated Mar. 17, 2014.
Kurt et al., "Tandem oral, rectal and nasal administrations of Ankaferd Blood Stopper to control profuse bleeding leading to hemodynamic instability," Am J. Emerg. Med. 27(5):631, e1-2 (2009).
Labhasetwar et al., "Arterial uptake of biodegradable nanoparticles: effect of surface modifications," Journal of Pharmaceutical Sciences, vol. 87, No. 10, 1229-1234 (1998).
Lamm et al., "Bladder Cancer: Current Optimal Intravesical Treatment: Pharmacologic Treatment," Urologic Nursing 25(5):323-6, 331-2 (Oct. 26, 2005).
Latella et al., "Nanoindentation hardness. Young's modulus, and creep behavior of organic-inorganic silica-based sol-gel thin films on copper," J Mater Res 23(9): 2357-2365 (2008).
Lawrence et al., "Rectal tacrolimus in the treatment of resistant ulcerative proctitis," Aliment. Pharmacol Ther. 28(10):1214-20 (2008).
Lee et al., "Novel therapy for hearing loss: delivery of insulin-like growth factor 1 to the cochlea using gelatin hydrogel,"Otol. Neurotol. 28(7):976-81 (2007).
Lehmann et al, "Drug treatment of nonviral sexually transmitted diseases: specific issues in adolescents," Pediatr Drugs 3(7):481-494 (2001).
Mahoney et al., "Three-Dimensional Compositional Analysis of Drug Eluting Stent Coatings Using Cluster Secondary Ion mass Spectrometry," Anal. Chem. 80:624-632 (2008).
Mario, C.D. et al., "Drug-Eluting Bioabsorbable Magnesium Stent," J. Interventional Cardiology 16(6):391-395 (2004).
Matsumoto, D, et al. Neointimal Coverage of Sirolimus-Eluting Stents at 6-month Follow-up: Evaluated by Optical Coherence Tomography, European Heart Journal, 28:961-967 (2006).
McAlpine, J.B. et al., "Revised NMR Assignments for Rapamycine," J. Antibiotics 44:688-690 (1991).
Mehik et al., "Alfuzosin treatment for chronic prostatitis/chronic pelvic pain syndrome: a prospecitve, randomized, double-blind, placebo-controlled, pilot study," Urology 62(3):425-429 (2003).
Mei et al., "Local Delivery of Modified Paclitaxel-Loaded Poly(ε-caprolactone)/Pluronic F68 Nanoparticles for Long-Term Inhibition of Hyperplasia," Journal of Pharmaceutical Sciences, Vol. 98, No. 6, (Jun. 2009).
Melonakos et al., Treatment of low-grade bulbar transitional cell carcinoma with urethral instillation of mitomycin C, Adv. Urol., 173694 Epub; (2008).
Merrett et al., "Interaction of corneal cells with transforming growth factor beta2-modified poly dimethyl siloxane surfaces," Journal of Biomedical Materials Research, Part A, vol. 67A, No. 3, pp. 981-993 (2003).
Merriam-Webster Online Dictionary, obtained online at: http://www.merriam-webster.com/dictionary/derivative, downloaded Jan. 23, 2013.
Middleton and Tipton, Synthetic biodegradable polymers as orthopedic devises. Biomaterials 21:2335-46 (2000).
Minchin, "Nanomedicine: sizing up targets with nanoparticles," Nature Nanotechnology, 33:12-13 (2008).
Minoque et al., "Laryngotracheal topicalization with lidocaine before intubation decreases the incidence of coughing on emergence from general anesthesia," Anesth. Analg. 99(4):1253-1257 (2004).
Mishima et al. "Microencapsulation of Proteins by Rapid Expansion of Supercritical Solution with a Nonsolvent," AIChE J. 46(4):857-65 (2000).
Mocco et al., "Pharos neurovascular intracranail stent: Elective use for a symptomatic stenosis refractory to medical therapy," Catheter Cardiovasc. Interv. (epub) (Mar. 2009).
Mollen et al., "Prevalence of tubo-ovarian abcess in adolescents diagnosed with pelvice inflammatory disease in a pediatric emergency department," Pediatr. Emerg. Care, 22(9): 621-625 (2006).
Moroni et al., "Post-ischemic brain damage:targeting PARP-1 within the ischemic neurovaschular units as a realistic avenue to stroke treatment," FEBS J. 276(1):36-45 (2009).
Muhlen et al., "Magnetic Resonance Imaging Contrast Agent Targeted Toward Activated Platelets Allows in Vivo Detection of Thrombosis and Monitoring of Thrombolysis Circulation," 118:258-267 (2008).
Murphy et al., "Chronic prostatitis: management strategies," Drugs 69(1): 71-84 (2009).
MX/a/2010/01148 Office Action dated Feb. 11, 2014.
NZ 588549 Examination Report dated Mar. 28, 2011.
NZ 600814 Examination Report dated Jun. 29, 2012.
O'Neil et al., "Extracellular matrix binding mixed micelles for drug delivery applications," Journal of Controlled Release 137:146-151 (2009).
O'Donnell et al., "Salvage intravesical therapy with interferon-alpha 2b plus low dose bacillus Calmette-Guerin alone perviously failed," Jour. Urology, 166(4):1300-1304 (2001).
Olbert et al., "In vitro and in vivo effects of CpG-Oligodeoxynucleotides (CpG-ODN) on murine transitional cell carcinoma and on the native murine urinary bladder wall," Anticancer Res. 29(6):2067-2076 (2009).
Ong and Serruys, "Technology Insight: an overview of research in drug-eluting stents," Nat. Clin. Parct. Cardiovas. Med. 2(12):647-658 (2005).
PCT/US06/24221 International Preliminary Report on Patentability dated Dec. 24, 2007.
PCT/US06/24221 International Search Report dated Jan. 29, 2007.
PCT/US06/27321 International Preliminary Report on Patentability dated Jan. 16, 2008.
PCT/US06/27321 International Search Report dated Oct. 16, 2007.
PCT/US06/27322 International Preliminary Report on Patentability dated Jan. 16, 2008.
PCT/US06/27322 International Search Report dated Apr. 25, 2007.
PCT/US07/10227 International Preliminary Report on Patentability dated Oct. 28, 2008.
PCT/US07/10227 International Search Report dated Aug. 8, 2008.

(56) References Cited

OTHER PUBLICATIONS

PCT/US07/80213 International Preliminary Report on Patentability dated Apr. 7, 2009.
PCT/US07/80213 International Search Report dated Apr. 16, 2008.
PCT/US07/82275 International Search Report dated Apr. 18, 2008.
PCT/US07/82775 International Preliminary Report on Patentablity dated Apr. 28, 2009.
PCT/US08/11852 International Preliminary Report on Patentability dated Apr. 20, 2010.
PCT/US08/11852 International Search Report dated Dec. 19, 2008.
PCT/US08/50536 International Preliminary Report on Patentability dated Jul. 14, 2009.
PCT/US08/50536 International Search Report dated Jun. 2, 2008.
PCT/US08/60671 International Preliminary Report on Patentability dated Oct. 20, 2009.
PCT/US08/60671 International Search Report dated Sep. 5, 2008.
PCT/US08/64732 International Preliminary Report on Patentability dated Dec. 1, 2009.
PCT/US08/64732 International Search Report dated Sep. 4, 2008.
PCT/US09/41045 International Preliminary Report on Patentability dated Oct. 19, 2010.
PCT/US09/41045 International Search Report dated Aug. 11, 2009.
PCT/US09/50883 International Preliminary Report on Patentability dated Jan. 18, 2011.
PCT/US09/50883 International Search Report dated Nov. 17, 2009.
PCT/US09/69603 International Preliminary Report on Patentability dated Jun. 29, 2011.
PCT/US09/69603 International Search Report dated Nov. 5, 2010.
PCT/US10/28195 International Preliminary Report on Patentability dated Sep. 27, 2011.
PCT/US10/28195 Search Report and Written Opinion dated Jan. 21, 2011.
PCT/US10/28253 International Preliminary Report on Patentability dated Sep. 27, 2011.
PCT/US10/28253 Search Report and Written Opinion dated Dec. 6, 2010.
PCT/US10/28265 International Report on Patentability dated Sep. 27, 2011.
PCT/US10/28265 Search Report and Written Opinion dated Dec. 3, 2010.
PCT/US10/29494 International Preliminary Report on Patentability dated Oct. 4, 2011.
PCT/US10/29494 Search Report and Written Opinion dated Feb. 7, 2011.
PCT/US10/31470 International Preliminary Report on Patentability dated Oct. 18, 2011.
PCT/US10/31470 Search Report and Written Opinion dated Jan. 28, 2011.
PCT/US10/42355 International Preliminary Report on Patentability dated Jan. 17, 2012.
PCT/US10/42355 Search Report dated Sep. 2, 2010.
PCT/US11/032371 International Report on Patentability dated Oct. 16, 2012.
PCT/US11/032371 International Search Report dated Jul. 7, 2011.
PCT/US11/044263 International Search Report, International Preliminary Report on Patentability and Written Opinion dated Feb. 9, 2012.
PCT/US11/051092 International Preliminary Report on Patentability dated Mar. 21, 2013.
PCT/US11/051092 International Search Report dated Mar. 27, 2012.
PCT/US11/051092 Written Opinion dated Mar. 27, 2012.
PCT/US11/22623 International Preliminary Report on Patentability dated Aug. 7, 2012.
PCT/US11/22623 Search Report and Written Opinion dated Mar. 28, 2011.
PCT/US11/29667 International Search Report and Written Opinion dated Jun. 1, 2011.
PCT/US11/67921 International Preliminary Report on Patentability dated Jul. 11, 2013.
PCT/US11/67921 Search Report and Written Opinion dated Jun. 22, 2012.
PCT/US12/040040 International Search Report dated Sep. 7, 2012.
PCT/US12/33367 International Preliminary Report on Patentability dated Oct. 15, 2013.
PCT/US12/33367 International Search Report dated Aug. 1, 2012.
PCT/US12/46545 International Search Report dated Nov. 20, 2012.
PCT/US12/50408 International Search Report dated Oct. 16, 2012.
PCT/US13/41466 International Search Report and Written Opinion dated Oct. 17, 2013.
PCT/US13/42093 International Search Report and Written Opinion dated Oct. 24, 2013.
PCT/US2011/033225 International Search Report and Written Opinion dated Jul. 7, 2011.
PCT/US2012/60896 International Search Report and Written Opinion dated Dec. 28, 2012.
PCT/US2013/065777 International Search Report and Written Opinion dated Jan. 29, 2014.
PCT/US2014/025017 International Search Report and Written Opinion dated Jul. 7, 2014.
Perry et al., Chemical Engineer's Handbook, 5th Edition, McGraw-Hill, New York, p. 20-106 (1973).
Plas et al., "Tubers and tumors: rapamycin therapy for benign and malignant tumors", Curr Opin Cell Bio 21: 230-236, (2009).
Poling et al., The Properties of Gases and Liquids. McGraw-Hill. 9:1-9.97 (2001).
Pontari, "Chronic prostatitis/chronic pelvic pain syndrome in elderly men: toward better understanding and treatment," Drugs Aging 20(15):1111-1115 (2003).
Pontari, "Inflammation and anti-inflammatory therapy in chronic prostatits," Urology 60(6Suppl):29-33 (2002).
Putkisto, K. et al. "Polymer Coating of Paper Using Dry Surface Treatment—Coating Structure and Performance", ePlace newsletter, vol. 1, No. 8, pp. 1-20 (2004).
Raganath et al., "Hydrogel matrix entrapping PLGA-paclitaxel microspheres: drug delivery with near zero-order release and implantability advantages for malignant brain tumour," Pharm Res (Epub) (Jun. 20, 2009).
Ranade et al., "Physical characterization of controlled release of paclitaxel from the TAXUS Express2 drug-eluting stent," J. Biomed Mater. Res. 71(4):625-634 (2004).
Reddy et al., "Inhibition of apoptosis through localized delivery of rapamycin-loaded nanoparticles prevented neointimal hyperplasia and reendothelialized injured artery," Circ Cardiovasc Interv 1:209-216 (2008).
Ristikankare et al., "Sedation, topical pharnygeal anesthesia and cardiorespiratory safety during gastroscopy," J. Clin Gastorenterol. 40(1):899-905 (2006).
Sahajanand, Medical Technologies (Supralimus Core; Jul. 6, 2008).
Salo et al., "Biofilm formation by *Escherichia coli* isolated from patients with urinary tract infections," Clin Nephrol. 71(5):501-507 (2009).
Saxena et al., "Haemodialysis catheter-related bloodstream infections: current treatment options and strategies for prevention," Swiss Med Wkly 135:127-138 (2005).
Schetsky, L. McDonald, "Shape Memory Alloys", Encyclopedia of Chemical Technology (3d Ed), John Wiley & Sons 20:726-736 (1982).
Scheuffler et al., "Crystal Structure of Human Bone Morphogenetic Protein-2 at 2.7 Angstrom resolution," Journal of Molecular Biology, vol. 287, Issue 1, Mar. 1999.
Schmidt et al., "A Comparison of the Mechanical Performance Characteristics of Seven Drug-Eluting Stent Systems," Catheterization and Cardiovascular Interventions 73:350-360 (2009).
Schmidt et al., "In vitro measurement of quality parameters of stent-catheter systems," Biomed Techn 50(S1):1505-1506 (2005).
Schmidt et al., "New aspects of in vitro testing of arterial stents based on the new European standard," EN 14299, [online] (2009), [retrieved on Mar. 10, 2001] http://www.lib0ev.de/pl/pdf/EN14299.pdf (2009).
Schmidt et al., "Trackability, Crossability, and Pushability of Coronary Stent Systems—An Experimental Approach," Biomed Techn 47:Erg. 1, S. 124-126 (2002).

(56) References Cited

OTHER PUBLICATIONS

Schreiber, S.L. et al., "Atomic Structure of the Rapamycin Human Immunophilin FKBP-12 Complex," J. Am. Chem. Soc. 113:7433-7435 (1991).
Sen et al., "Topical heparin: A promising agent for the prevention of tracheal stenosis in airway surgery," J. Surg. Res (Epub ahead of print) (Feb. 21, 2009).
Serruys, Patrick et al., Comparison of Coronary-Artery Bypass Surgery and Stenting for the Treatment of Multivessel Disease, N. Engl. J. Med., vol. 344, No. 15, pp. 1117-1124 (2001).
SG201007602-4 Examination Report dated Feb. 13, 2013.
SG201007602-4 Written Opinion dated May 25, 2012.
Shekunov et al. "Crystallization Processes in Pharmaceutical Technology and Drug Delivery Design." Journal of Crystal Growth 211:122-136 (2000).
Simpson et al., "Hyaluronan and hyaluronidase in genitourinary tumors." Front Biosci. 13:5664-5680 (2008).
Smith et al., "Mitomycin C and the endoscopic treatment of laryngotracheal stenosis: are two applications better than one?" Laryngoscope 119(2):272-283 (2009).
Sumathi et al., "Controlled comparison between betamethasone gel and lidocaine jelly applied over tracheal tube to reduce postoperative sore throat, cough, and hoarseness of voice," Br. J. Anaesth. 100(2):215-218 (2008).
Szabadits et al., "Flexibility and trackability of laser cut coronary stent systems," Acta of Bioengineering and Biomechanics 11(3):11-18 (2009).
Testa, B. Prodrug research: futile or fertile? Biochem Pharmacol. 1:68(11):2097-106 (2004).
Thalmann et al., "Long-term experience with bacillus Calmette-Guerin therapy of upper urinary tract transitional cell carcinoma in patients not eligible for surgery," J Urol. 168(4 Pt 1):1381-1385 (2002).
Torchilin, "Micellar Nanocarriers: Pharmaecutial Perspectives," Pharmaceutical Research, vol. 24, No. 1, 17 pages (2007).
U.S. Appl. No. 11/158,724 Office Action dated Dec. 31, 2013.
U.S. Appl. No. 11/158,724 Office Action dated May 23, 2013.
U.S. Appl. No. 11/158,724 Office Action dated Sep. 17, 2009.
U.S. Appl. No. 11/158,724 Office Action dated Sep. 26, 2012.
U.S. Appl. No. 11/158,724 Office Action dated Sep. 8, 2008.
U.S. Appl. No. 11/158,724 Office Action dated Jun. 25, 2014.
U.S. Appl. No. 11/877,591 Final Office Action dated Nov. 4, 2013.
U.S. Appl. No. 11/877,591 Office Action dated Feb. 29, 2012.
U.S. Appl. No. 11/877,591 Office Action dated Jul. 1, 2013.
U.S. Appl. No. 11/877,591 Office Action dated Sep. 21, 2012.
U.S. Appl. No. 11/877,591 Office Action dated May 7, 2014.
U.S. Appl. No. 11/995,685 Office Action dated Aug. 20, 2010.
U.S. Appl. No. 11/995,685 Office Action dated Nov. 24, 2009.
U.S. Appl. No. 11/995,687 Office Action dated Apr. 6, 2012.
U.S. Appl. No. 11/995,687 Office Action dated Sep. 28, 2011.
U.S. Appl. No. 12/298,459 Office Action dated Apr. 6, 2012.
U.S. Appl. No. 12/298,459 Office Action dated Aug. 10, 2011.
U.S. Appl. No. 12/298,459 Office Action dated May 31, 2013.
U.S. Appl. No. 12/426,198 Office Action dated Feb. 6, 2012.
U.S. Appl. No. 12/426,198 Office Action dated Feb. 7, 2014.
U.S. Appl. No. 12/426,198 Office Action dated Mar. 23, 2011.
U.S. Appl. No. 12/443,959 Office Action dated Dec. 13, 2012.
U.S. Appl. No. 12/443,959 Office Action dated Feb. 15, 2012.
U.S. Appl. No. 12/504,597 Final Office Action dated Oct. 3, 2012.
U.S. Appl. No. 12/504,597 Office Action dated Apr. 1, 2014.
U.S. Appl. No. 12/504,597 Office Action dated Dec. 5, 2011.
U.S. Appl. No. 12/522,379 Office Action dated Apr. 8, 2014.
U.S. Appl. No. 12/522,379 Final Office Action dated Aug. 28, 2013.
U.S. Appl. No. 12/522,379 Office Action dated Dec. 26, 2012.
U.S. Appl. No. 12/595,848 Office Action dated Jan. 13, 2012.
U.S. Appl. No. 12/595,848 Office Action dated Mar. 15, 2013.
U.S. Appl. No. 12/595,848 Office Action dated Oct. 22, 2013.
U.S. Appl. No. 12/595,848 Office Action dated Jun. 3, 2014.
U.S. Appl. No. 12/601,101 Office Action dated Dec. 27, 2012.
U.S. Appl. No. 12/601,101 Office Action dated Feb. 13, 2014.
U.S. Appl. No. 12/601,101 Office Action dated Mar. 27, 2012.
U.S. Appl. No. 12/601,101 Office Action dated May 22, 2013.
U.S. Appl. No. 12/648,106 Final Office Action dated Sep. 25, 2012.
U.S. Appl. No. 12/648,106 Office Action dated Jan. 30, 2012.
U.S. Appl. No. 12/648,106 Office Action dated Sep. 18, 2013.
U.S. Appl. No. 12/729,156 Final Office Action dated Oct. 16, 2012.
U.S. Appl. No. 12/729,156 Office Action dated Feb. 1, 2012.
U.S. Appl. No. 12/729,156 Office Action dated Feb. 13, 2014.
U.S. Appl. No. 12/729,156 Office action dated May 8, 2013.
U.S. Appl. No. 12/729,580 Final Office Action dated Nov. 14, 2013.
U.S. Appl. No. 12/729,580 Office Action dated Apr. 10, 2012.
U.S. Appl. No. 12/729,580 Office Action dated Jan. 22, 2013.
U.S. Appl. No. 12/729,580 Office Action dated Sep. 10, 2014.
U.S. Appl. No. 12/729,603 Final Office Action dated Oct. 10, 2012.
U.S. Appl. No. 12/729,603 Office Action dated Mar. 27, 2012.
U.S. Appl. No. 12/729,603 Office Action dated Jun. 25, 2014.
U.S. Appl. No. 12/738,411 Final Office Action dated Apr. 11, 2013.
U.S. Appl. No. 12/738,411 Office Action dated Aug. 21, 2013.
U.S. Appl. No. 12/738,411 Office Action dated Feb. 6, 2014.
U.S. Appl. No. 12/738,411 Office Action dated May 30, 2014.
U.S. Appl. No. 12/748,134 Office Action dated Jul. 18, 2013.
U.S. Appl. No. 12/751,902 Office Action dated Dec. 19, 2013.
U.S. Appl. No. 12/751,902 Office Action dated Jul. 13, 2012.
U.S. Appl. No. 12/762,007 Final Office Action dated Oct. 22, 2013.
U.S. Appl. No. 12/762,007 Final Office Action dated Apr. 30, 2014.
U.S. Appl. No. 12/762,007 Office Action dated Feb. 11, 2013.
U.S. Appl. No. 13/014,632 Office Action dated Jan. 10, 2014.
U.S. Appl. No. 13/014,632 Office Action dated May 8, 2013.
U.S. Appl. No. 13/086,335 Office Action dated May 22, 2013.
U.S. Appl. No. 13/086,335 Office Action dated Apr. 4, 2014.
U.S. Appl. No. 13/229,473 Office Action dated Jun. 17, 2013.
U.S. Appl. No. 13/340,472 Office Action dated Apr. 26, 2013.
U.S. Appl. No. 13/340,472 Office Action dated Jan. 15, 2014.
U.S. Appl. No. 13/340,472 Office Action dated Aug. 29, 2014.
U.S. Appl. No. 13/384,216 Final Action dated Nov. 6, 2013.
U.S. Appl. No. 13/384,216 Office Action dated Apr. 24, 2013.
U.S. Appl. No. 13/605,904 Office Action dated Jun. 28, 2013.
U.S. Appl. No. 13/605,904 Office Action dated Nov. 27, 2012.
U.S. Appl. No. 13/445,723 Office Action dated Mar. 14, 2014.
U.S. Appl. No. 13/090,525 Office Action dated Apr. 11, 2014.
U.S. Appl. No. 11/995,685 Office Action dated Jun. 18, 2014.
Unger et al., "Poly(ethylene carbonate): A thermoelastic and biodegradable biomaterial for drug eluting stent coatings?" Journal of Controlled Release, vol. 117, Issue 3, 312-321 (2007).
Verma et al., "Effect of surface properties on nanoparticle-cell interactions," Small 6(1):12-21 (2010).
Wagenlehner et al., "A pollen extract (Cernilton) in patients with inflammatory chronic prostatitis/chronic pelvic pain syndrome: a multicentre, randomized, prospective, double-blind, placebo-controlled phase 3 study," Eur Urol 9 (Epub) (Jun. 3, 2009).
Wang et al. Controlled release of sirolimus from a multilayered PLGA stent matrix. Biomaterials 27:5588-95 (2000).
Wang et al., "Treatment with melagatran alone or in combination with thrombolytic therapy reduced ischemic brain injury," Exp. Neurol 213(1):171-175 (2008).
Warner et al., "Mitomycin C and airway surgery: how well does it work?" Ontolaryngol Head Neck Surg. 138(6):700-709 (2008).
Wermuth, CG Similarity in drugs: reflections on analogue design. Drug Discov Today. 11(7-8):348-54. (2006).
Witjes et al., "Intravesical pharmacotherapy for non-muscle-invasive bladder cancer: a critical analysis of currently available drugs, treatment schedules, and long-term results," Eur. Urol. 53(1):45-52 (2008).
Wu et al., "Study on the preparation and characterization of biodegradable polylactide/multi-walled carbon nanotubes nanocomposites." Polymer 48: 4449-4458 (2007).
Xu et al., "Biodegradation of poly(l-lactide-co-glycolide tube stents in bile" Polymer Degradation and Stability. 93:811-817 (2008).
Xue et al., "Spray-as-you-go airway topical anesthesia in patients with a difficult airway: a randomized, double-blind comparison of 2% and 4% lidocaine," Anesth. Analg. 108(2): 536-543 (2009).

(56) References Cited

OTHER PUBLICATIONS

Yepes et al., "Tissue-type plasminogen activator in the ischemic brain: more than a thrombolytic," Trends Neurosci. 32(1):48-55 (2009).
Yousof et al., "Reveratrol exerts its neuroprotective effect by modulating mitochondrial dysfunction and associated cell death during cerebral ischemia," Brain Res. 1250:242-253 (2009).
Zhou et al. Synthesis and Characterization of Biodegradable Low Molecular Weight Aliphatic Polyesters and Their Use in Protein-Delivery Systems. J Appl Polym Sci 91:1848-56 (2004).
Zilberman et al., Drug-Eluting bioresorbable stents for various applications, Annu Rev Biomed Eng., 8:158-180 (2006).
PCT/US11/44263 International Search Report and Written Opinion dated Feb. 9, 2012.
Charging of Materials and Transport of Charged Particles (Wiley Encyclopedia of Electrical and Electronics Engineering, John G. Webster (Editor), vol. 7, 1999, John Wiley & Sons, Inc., pp. 20-24).
The Properties of Gases and Liquids, 5th ed., McGraw-Hill, Chapter 9, pp. 9.1-951, 2001.
Klein et al., Viscosities of pure gases can vary by as much as a factor of 5 depending upon the gas type, Int. J. Refrigeration 20: 208-217, 1997.

\* cited by examiner

SYSTEM AND PROCESS FOR FORMATION OF A TIME-RELEASED, DRUG-ELUTING TRANSFERABLE COATING

CROSS-REFERENCE

This application claims the benefit of U.S. Provisional Application No. 61/491,847, filed May 31, 2011 and U.S. Provisional Application No. 61/649,585, filed May 21, 2012, each of which are incorporated herein by reference in their entirety.

FIELD OF THE INVENTION

The present invention relates generally to preparation of composite coatings. More particularly, the invention relates to a system and process for forming transferable coatings on expandable medical devices that upon deployment within a patient or host yield time-released, drug-eluting coatings for treatment of medical conditions.

BACKGROUND OF THE INVENTION

Expandable medical balloons have conventionally been used in the medical arts to open up plaque-restricted vessels by compressing the plaque that has accumulated within the vessel. However, in the process of expansion, these vessels can be damaged at the point of deployment of the medical balloons. Further, to date, conventional balloon technologies have been unable to provide any delivery of drugs over time to tissues damaged by the balloon expansion or the resulting distension of vessel walls. And, while stents have been used to deliver drugs within a patient over a period of time, the stents must remain in the patient for the period over which the drug delivery occurs, which can be problematic as the body responds to the presence of the stent. Accordingly, new devices and methods are needed that can deliver drugs over time in a patient that provide medical intervention without the need for the delivery device to remain in the patient.

SUMMARY OF THE INVENTION

Figure 1:
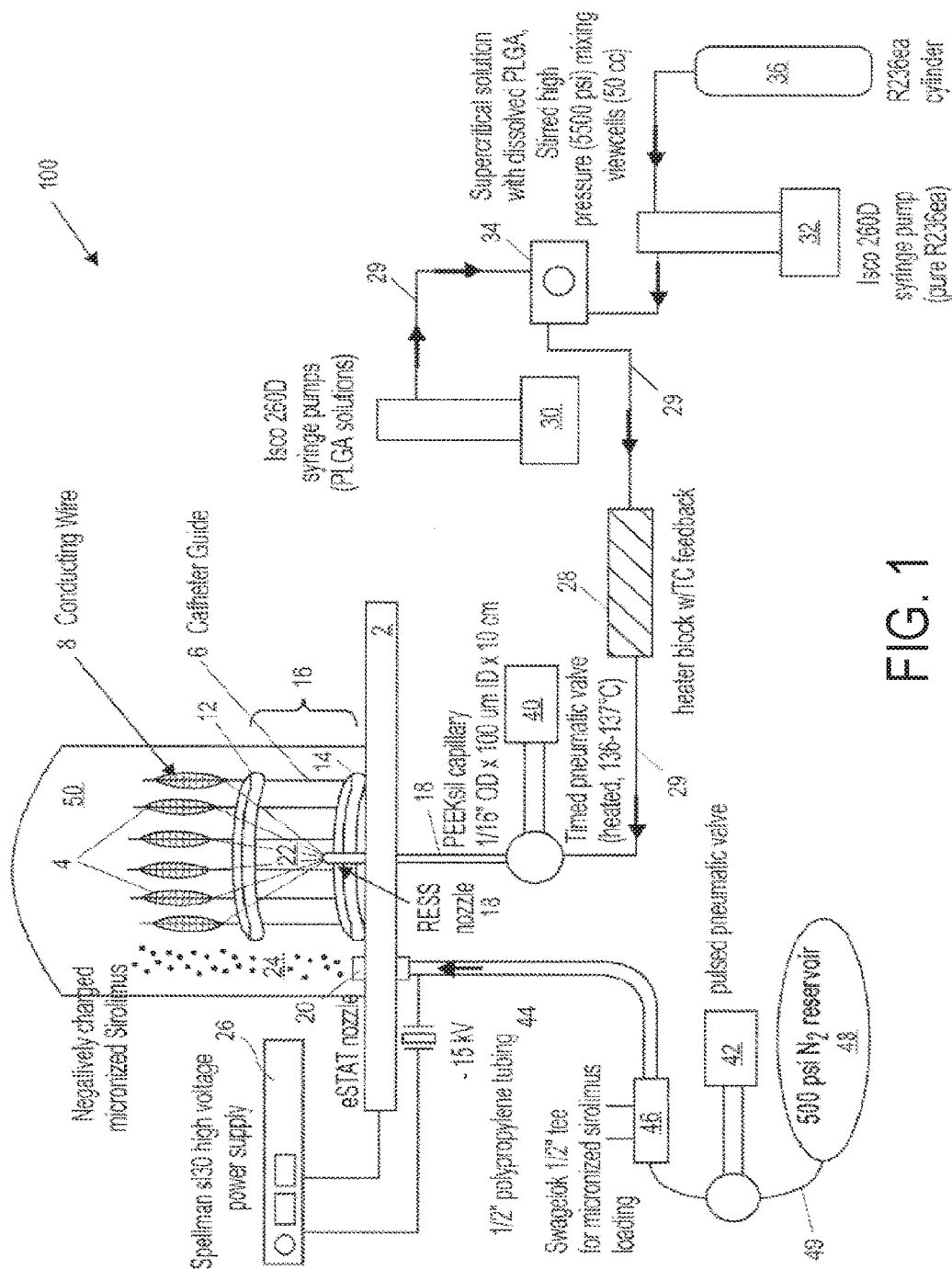
FIG. 1 shows a system for formation of transferable coatings on the surface of expandable medical devices, according to an embodiment of the invention.

In its simplest form, the present invention includes a system and process for forming composite coatings on expandable medical devices that, upon deployment within a patient or host, transfer time-released, drug-eluting deposits at selected sites within the patient that deliver treatments for various medical conditions. In various embodiments, preparation of drug-eluting coatings on balloon surfaces is detailed including modifications that allow transfer of the drug-eluting coatings within target vessels where medical intervention is needed for treatment, that results in the formation of the time-released, drug-eluting coatings therein.

In various embodiments, particles that yield the coating layers include various materials including polymers, drugs, and polymer/drug combinations detailed herein.

The present invention also includes a process for modifying the surface of the composite coating that contains, e.g., time-released drugs that allows delivery of the material within the coating from the surface of the medical balloon to a target location within the patient, which forms a time-released, drug-eluting deposit of material at the target location. Formation of these drug-eluting deposits and deployment from expandable medical balloons to the actual host vessels (e.g., heart) has been demonstrated.

The purpose of the foregoing abstract is to enable the United States Patent and Trademark Office and the public generally, especially scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Various advantages and novel features of the present invention are described herein and will be readily apparent to those skilled in this art from the following detailed description. In the preceding and following descriptions the preferred embodiment of the invention is shown and described by way of illustration of the best mode contemplated for carrying out the invention. As will be realized, the invention is capable of modification in various respects without departing from the invention. These and other enhancements and applications are described further herein.

The following description includes detail of the preferred best mode of one embodiment of the present invention. It will be clear from this description of the invention that the invention is not limited to these illustrated embodiments. The person of ordinary skill in the art will recognize that the invention is susceptible of various modifications and alternative constructions. Therefore the present description should be seen as illustrative and not limiting. It should further be understood that there is no intention to limit the invention to the specific form disclosed, but on the contrary, the invention is to cover all modifications, alternative constructions, and equivalents falling within scope of the invention as defined in the claims. Accordingly, the drawings and description should be seen as illustrative of the invention and not as limiting in any way.

Provided herein is a method for forming an implantable, drug-eluting coating on the surface of an expandable medical device, characterized by the steps of: mounting an expandable delivery device with an internally disposed conducting member that maximizes conduction of charge on the surface of the device; delivering preselected potentials with the conducting member to the surface of the expandable delivery device to maximize collection of coating particles on the surface thereof; and coating the expandable delivery device with coating particles delivered via an e-RESS process, and e-STAT process, or a combined e-RESS process and e-STAT process to form one or more coating layers on the surface thereof.

In some embodiments, the expandable delivery device is a medical balloon. In some embodiments, at least one coating layer of the expandable delivery device includes a drug-eluting component and at least one coating layer includes a biosorbable polymer forming the implantable drug eluting coating on the surface of the device. In some embodiments, the medical balloon comprises nylon.

In some embodiments, the coating provides transfer of at least a portion of the one or more coating layers upon contact with a host vessel.

In some embodiments, wherein the expandable delivery device is at least a portion of a medical implant device. In some embodiments, the expandable delivery device is an interventional device. In some embodiments, the expandable delivery device is a diagnostic device. In some embodiments, the expandable delivery device is mounted to a delivery device prior to insertion into a host vessel. In some embodiments, the delivery device is a catheter.

In some embodiments, the conduction of charge on the surface is via gas-phase conduction or surface conduction of charge. In some embodiments, the delivering of preselected potentials includes delivering an active potential with the conducting component. In some embodiments, the delivering of preselected potentials does not include applying an active potential to the conducting component. In some embodiments, the delivering includes applying an electrostatic field potential on the surface of the expandable delivery device of at least about 15 kV prior to the coating step with the e-STAT process.

In some embodiments, the biosorbable polymer and drug eluting component are located within the same coating layer. In some embodiments, the coating includes coating the surface simultaneously with the e-RESS process and the e-STAT process to encapsulate a drug and a biosorbable polymer in a single layer of the drug-eluting coating.

In some embodiments, the drug-eluting component includes a drug dispersed within a biosorbable polymer disposed in a single coating layer. In some embodiments, the biosorbable polymer and drug-eluting component are located in different coating layers. In some embodiments, at least one coating layer includes a binding component comprising polylactoglycolic acid (PLGA).

In some embodiments, the expandable delivery device is at least partially expanded during coating of same.

In some embodiments, at least a portion of the biosorbable polymer has a preselected molecular weight that enhances transferability of the drug-eluting coating to the receiving surface within the host vessel. In some embodiments, the drug is a time-released drug that provides time-selectivity for treatment of a host or patient. In some embodiments, the drug has a crystalline form. In some embodiments, the drug comprises sirolimus.

In some embodiments, the coating includes masking one or more preselected portions of the expandable delivery device. In some embodiments, the masking includes forming preselected shapes selected from: oval, square, rectangle, triangular, or cylindrical within the coating layers on the surface of the expandable delivery device that contain an active drug delivered in the drug-eluting coating when in contact with the receiving surface.

In some embodiments, at least one coating layer includes a releasing agent selected from the group consisting of hydrophilic or hydrophobic chemicals or polymers that lower the interfacial energy between the surface of the medical device and the coating layers, water soluble chemicals or polymers that dissolve to eliminate adhesion between coatings layers and the medical device surface, brittle or friable coatings that lose mechanical cohesion upon, polyethylene glycols (PEG), hydrogels, polyesters, polyacrylates, polysaccharides, silicones, silanes, tocopherol, glycerin, sucrose, cellulose, shellac, and combinations thereof providing release of the coating to the receiving surface upon contact with same. In some embodiments, the releasing agent is located within a coating layer disposed between the surface of the expandable delivery device and a first layer comprising a biosorbable polymer.

In some embodiments, at least one coating layer on the surface of the expandable delivery device comprises a low-energy releasing agent selected from the group consisting of a releasing agent with surface energy of less than 35 dynes/cm or agents onto which a drop of water would experience a contact angle of greater than 90 degrees, polyvinyl alcohols (PVA), ethylene vinyl acetates (EVA), folyolefins, fluorosilanes, fluoroacrylates, fluorohydrocarbons, paraffin, long chain hydrocarbons, and combinations thereof. In some embodiments, the low-energy releasing agent is located within a coating layer disposed between the surface of the expandable delivery device and a first layer comprising a biosorbable polymer.

In some embodiments, at least one coating layer on the surface of the expandable delivery device comprises an adhesive agent selected from the group consisting of agents with cationic moieties that assist in cellular adhesion/uptake, shattering agents that penetrate tissue surface and promote adhesion through mechanical entanglement, viscous polymeric agents, and cationic polyamino acids such as polyarginine, polylysine, polyhistidine, and polyethyleneimine (PEI), 3,4-dihydroxy-L-phenylalanine (dopa), (as in active component in mussel adhesive), laminins, cationic surfactant molecules such as didodecyldimethylammonium bromide (DMAB), ethylhexadecyldimethylammonium bromide, dodecyltrimethyl ammonium bromide, tetradodecylammonium bromide, dimethylditetradecylammonium bromide, detrabutylammonium iodide, DEAE-dextran hydrochloride, and hexadimethrine bromide, and combinations thereof that affixes the transferable coating material to the receiving surface upon expansion of the expandable delivery device. In some embodiments, the transferable coating material includes an adhesion layer that enhances adhesion with the receiving surface. In some embodiments, the adhesive agent is included with the biosorbable polymer in a single coating layer on the surface of the expandable delivery device.

In some embodiments, at least one coating layer includes both the biosorbable polymer and a drug or therapeutic agent to provide timed-release delivery of the drug or therapeutic agent by dissolution of the biosorbable polymer layer within the coating material transferred to the host vessel. In some embodiments, the leading layer of the transferable coating on the surface of the expandable delivery device contains therapeutic drug particles modified with a surface charge prior.

In some embodiments, the coating particles are of a size between about 0.01 micrometers and about 10 micrometers.

In some embodiments, the step of sintering the transferable coating material to form a dense, thermally stable film on the surface of the expandable delivery device prior to delivery of same at a temperature in the range from about 25° C. to about 150° C.

In some embodiments, the sintering includes sintering the transferable coating material in the presence of a solvent gas to form a dense, thermally stable film on the surface of the expandable delivery device.

In some embodiments, the method further includes the step of transferring at least a portion of the coating from the expandable delivery device to a receiving surface of a host vessel to form a drug-eluting deposit therein. In some embodiments, the transferring includes expanding the expandable delivery device to transfer and implant at least a portion of the drug-eluting coating to the receiving surface of the host vessel. In some embodiments, the step of expanding includes expanding the expandable delivery device using a fluid that maintains rigidity and integrity of along the external surface of same. In some embodiments, the expanding includes at least partially deflating the expandable delivery device to reduce the physical dimensions of the expandable delivery device when inserting same into the host vessel prior to transferring the coating to the receiving surface of the host vessel.

Provided herein are devices comprising the elements noted herein, which may be produced according to methods described herein.

DETAILED DESCRIPTION

A system and process are detailed for forming composite coatings of transferable material on the surface of expandable medical devices. While various embodiments of the invention will be described in reference to coating of expandable medical balloons, the invention is not intended to be limited thereto. For example, the invention is applicable to any of a variety of expandable medical devices. Thus, no limitations are intended. The invention finds application in medical intervention technologies wherein medical catheters and stents are routinely deployed including, e.g., medical angioplasty and treatment of vascular conditions. For example, these composite coatings of transferable material are deployed at various target locations within the vascular system of a patient or host by activation (i.e., expansion) of the expandable device. The term "coating" as used herein means at least one layer containing a selected material or materials (e.g., preselected drugs and polymers) of a selected thickness that extends over at least a portion of the surface of the expandable medical device. Once the material from the composite coating is transferred or otherwise implanted at the site of delivery within the patient or host, the expandable medical device is removed. The transferred material then delivers, e.g., time-released drugs that provide medical intervention at the site of delivery without the device remaining in the patient or host. The present invention provides benefits for delivery of drugs not achieved with prior art devices including, but not limited to, e.g., preparation of composite coatings of transferable materials onto the surface of expandable medical delivery devices, transfer of the composite material from the surface of the medical balloon to the target location within the host vessel, implantation of the transferable material that forms the time-released drug-eluting deposite within the patient or host, and removal of the expandable medical device once the material is transferred into the patient or host. At least some portion of the drug-eluting deposit remains at the target site providing delivery of the time-released drug for the term of treatment without the medical delivery device remaining in the patient or host. Composite coatings comprising one or more layers of selected materials are formed on the surface of individual medical balloons by electrostatic collection of coating particles.

FIG. 1 is a schematic showing a coating system 100 for coating expandable medical balloon devices 4, according to one embodiment of the invention. System 100 includes a coating chamber 50 that mounts to a coating delivery stage 2. Coating delivery stage 2 is configured to deliver respective e-STAT and e-RESS coating particles generated in processes e-RESS plumes 22 and e-STAT plumes 4, described herein. e-RESS is a process by which electrostatically charged coating particles of a selected size (between about 5 µm to about 100 nm) are delivered by Rapid Expansion of Supercritical Solution (RESS) and electrostatically collected to form one or more coating layers on the surface of medical balloon 4. The e-RESS process is detailed in U.S. Pat. Nos. 4,582,731; 4,734,227; 4,734,451; 6,749,902; and 6,756,084 assigned to Battelle Memorial Institute (Richland, Wash.), which patents are incorporated herein in their entirety. e-STAT is a process by which dry coating particles of a selected size (between about 0.1 µm to about 10 µm) are delivered by abrupt entrainment of the solid particles in a carrier gas without use of an expansion fluid or delivery solvent. The particles are electrostatically collected to form one or more coating layers on the surface on the medical balloon devices 4. The e-STAT process is detailed in patent publication number WO 2007/011707 A2 (assigned to Battelle Memorial Institute, Richland, Wash., USA, and MiCell Technologies, Inc., Raleigh, N.C., USA), which reference is incorporated herein in its entirety. The e-RESS and e-STAT processes can be performed either sequentially (i.e., first one and then the other), or concurrently (i.e., simultaneously) to form any number of individual coating layers or to provide unique combinations and concentrations of materials in a single coating layer. Any combination or sequence of e-RESS and e-STAT steps may be used to produce a coating. The e-RESS process for forming coating particles is preferred for delivery of materials that are soluble in a supercritical fluid or other solvent and where micrometer-scale (or smaller diameter) particles are desirable or where other particle types are generated. For example, rapid nucleation occurs during the RESS process and typically leads to formation of amorphous or non-crystalline nanoparticles. The e-STAT process is preferred when delivery of particles is desired which are insoluble in a supercritical fluid solvent, or when a solution or solvent may alter the desirable physical or chemical properties of the particles, as when, e.g., highly crystalline particles are desired or need to be collected. Both processes can be used together in cases where combinations of particles with different properties or solubilities are desired or when different particles must be co-collected to form a single coating layer. Thus, no limitations are intended to exemplary embodiments. Coating layers composed of these various e-RESS and/or e-STAT coating particles are generated and deposited on the surface of the medical balloons forming coating layers, as detailed hereafter.

In the instant embodiment, an e-STAT delivery nozzle 20 is positioned adjacent to, and apart from, the e-RESS delivery nozzle 18, but positioning of delivery nozzles 18 and 20 nozzles is not limited. In a preferred embodiment, chamber 50 includes a balloon mounting assembly 16 of a dual ring type that circumvolves the e-RESS delivery nozzle 18. Balloon mounting assembly 16 includes an upper staging ring 12 and a lower (base) staging ring 14 that provide an equal separation distance between delivery nozzle 18 and balloons 4 mounted in upper staging ring 12 of stage 16.

Ring 12 also provides a suitable separation distance between adjacent medical balloons 4 for coating. Separation distance between balloons 4 is variable and need only be sufficient to prevent interference with electric fields that effect the electrostatic collection of e-RESS and e-STAT particles. Medical balloons 4 are preferably of an "over-the-wire" catheter type that include an inner guide wire (not shown) covered by a sleeve (not shown) internal to balloon 4, forming a tube-within-a-balloon or a sleeve-within-a-balloon arrangement, described further herein. e-RESS nozzle 18 couples to a cylinder 36 filled with a preselected solvent (e.g., R236ea). e-RESS nozzle 18 sprays a coating material in a supercritical solvent that expands as a plume 24 of electrostatically charged coating particles that collect on the surface of the medical balloons 4 mounted in mounting assembly 16. In the instant embodiment, solvent is delivered via syringe pump 32 and mixed in a high pressure cell 34 (e.g., 50 cm³ cell volume) with a $2^{nd}$ material (e.g. PLGA polymer) and the resulting mixed coating solution is delivered via syringe pump 30 through a heated block 28 configured with temperature control feedback at a high pressure (e.g., 5500 psi), forming the supercritical solution containing the mixed materials. Pressure is maintained within the delivery system by passing solution through the small diameter (e.g., 50 μm to 200 μm) e-RESS nozzle 18.

In the figure, the e-RESS nozzle 18 consists of a length of capillary tubing (exemplary dimensions: 100 μm I.D.×1/16$^{th}$ inch O.D.×10 cm) constructed of, e.g., a thermoplastic polymer [e.g., polyether ether ketone also known as PEEK® (Victrex USA, Inc., West Conshohocken, Pa., USA], but is not limited thereto. For example, other capillary materials may be used including, but not limited to, e.g., stainless steel. The nozzle materials may also be preformed, e.g., of sapphire. Thus, no limitations are intended. In the exemplary embodiment, RESS nozzle 18 (comprising, e.g., PEEK® tubing) is encased in stainless steel (e.g., ¼" OD stainless steel tubing) that is grounded to establish a uniform electric field over each balloon 4 mounted to mounting assembly 16. Pressure drops continuously over the length of the nozzle (capillary) 18. The supercritical coating solution is delivered through e-RESS nozzle 18 as a plume 22 of coating particles in conjunction with a timed pneumatic valve 40 at a preselected pressure (e.g., 5500 psi) and a preselected temperature (e.g., 150° C.). The expanded e-RESS solution produces dry coating particles (e.g., of a solute polymer) of a preselected size in a plume 22 of solvent gas. The solute particles then are electrostatically collected on the surface of the medical balloons, forming a coating layer. In exemplary tests, coating particles were generated by expansion of a near-critical or a supercritical solution prepared using a hydrofluorocarbon solvent, (e.g., fluoropropane R-236ea, Dyneon, Oakdale, Minn., USA) that further contained a dissolved biosorbable polymer [e.g., a 50:50 poly(DL-lactide-co-glycolide) (PLGA)] available commercially (Catalog No. B6010-2P, LACTEL® Absorbable Polymers, a division of Durect, Corp., Pelham, Ala., USA). In the instant tests, the supercritical solution delivered at 5500 psi and 150° C. through the expansion nozzle 18 was expanded into ambient (i.e., STP) conditions, but is not limited thereto. For example, delivery of RESS coating particles may be made at various pressures and temperatures.

In the e-STAT process, e-STAT orifice 20 delivers dry coating particles in a plume 24 in the absence of a supercritical solvent to the surfaces of medical balloons 4 in mounting assembly 16. In the instant embodiment, e-STAT orifice 20 is constructed from a modified bulkhead union (e.g., ½-inch SWAGELOK®) composed of a plastic material (e.g., nylon), but is not limited thereto. e-STAT orifice 20 is not charged. e-STAT orifice 20 couples to a reservoir 46 filled with a preselected drug (e.g., Sirolimus) or other coating material in a crystalline or dry powder form with particles preferably of a size in the range from about 10 μm to about 10 nm, but is not limited thereto. The drug or coating material in dry form is provided to e-STAT nozzle 20 through tubing 44 (e.g., ½ inch polypropylene or another polymeric tubing). Drug reservoir 46 containing the dry coating powder couples to a pneumatic valve 42 that delivers the dry coating particles as a plume 24 through the connecting tubing 44 and the e-STAT orifice 20 into the containment vessel 50 at a preselected pressure (e.g., 500 psi nitrogen) and temperature where particles are electrostatically collected on the surface of the medical balloons 4 mounted in mounting assembly 16. Pressures at which dry coating particles are delivered are not limited. Pneumatic valve 42 further couples to a gas reservoir 48 containing an inert gas (e.g., $N_2$) via tubing 49 that provides a discharging gas to pneumatic valve 42. In e-STAT processing of coatings for biomedical balloon applications, metal-containing guide wires 8 encased within the inner sleeve of the balloon 4 are charged with voltages that range preferably from about 5 kV to about 25 kV. More particularly, voltages range from about 10 kV to about 20 kV.

For combined e-RESS and e-STAT coating processes, delivery conditions are those described previously herein for the individual RESS and STAT processes, but the processes are performed simultaneously. Thus, the disclosure is not intended to be limited by the descriptions to the individual e-RESS and e-STAT processes.

Figure 2:
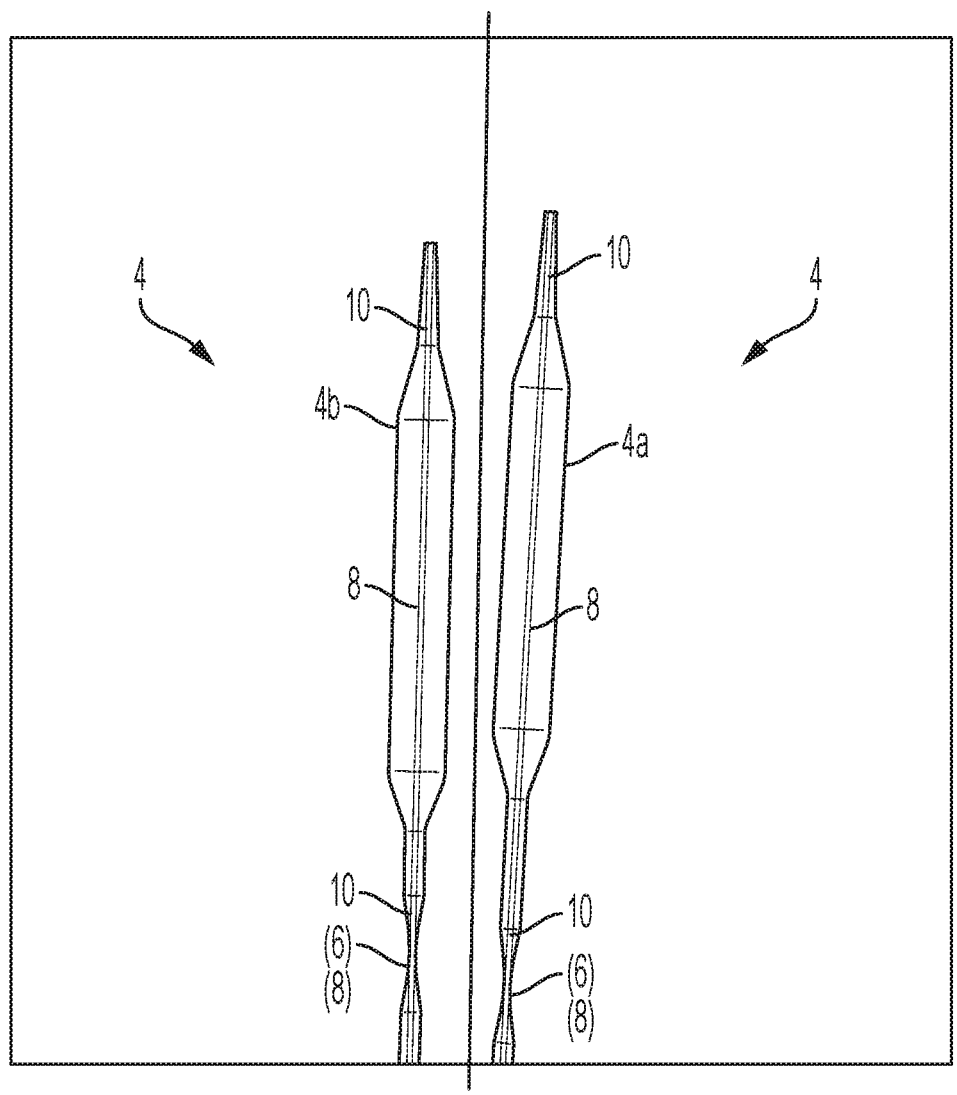
FIG. 2 shows two expandable balloons of an "over-the-wire" catheter type used in accordance with the invention.

FIG. 2 shows two medical balloons 4 of an "over-the-wire" catheter type coated in conjunction with one embodiment of the invention. In the figure, medical balloons 4 each include a catheter guide 6 through which a metal guide (conducting) wire 8 passes. Guide wire 8 passes through the center of each balloon 4 in a sleeve 10 that runs the length of balloon 4. The sleeve-within-the balloon configuration separates sleeve 10 from the expansion volume of each balloon 4. Sleeve 10 and balloon 4 are fused at either end of the balloon 4, forming a seal that allows for inflation of balloon 4 by introducing expansion gas through catheter guide 6. In the test configuration, balloons 4 were expanded by means of, e.g., a syringe coupled to a luer connection described hereafter positioned at the end of each catheter guide 6 distal to the expandable balloon 4, but the mechanism for expansion of balloons is not limited thereto. For example, a pneumatic pressure system may also be used, e.g., for production scale processing. Thus, no limitations are intended. In one balloon (on the right) of FIG. 2, metal guide wire 8 in balloon 4 was inserted to the tip of balloon 4 without protruding from the upper end (i.e., the normal coating condition). In the other balloon (on the left) of FIG. 2, balloon 4, guide wire 8 was retracted to below the mid section of balloon 4 prior to coating. Results in each image demonstrate that the coating on balloon 4 covers an area equal to the terminal position of guide wire 8 in sleeve 10, illustrating the effect the guide wire 8 has on collection efficiency of the coating materials.

Figure 3:
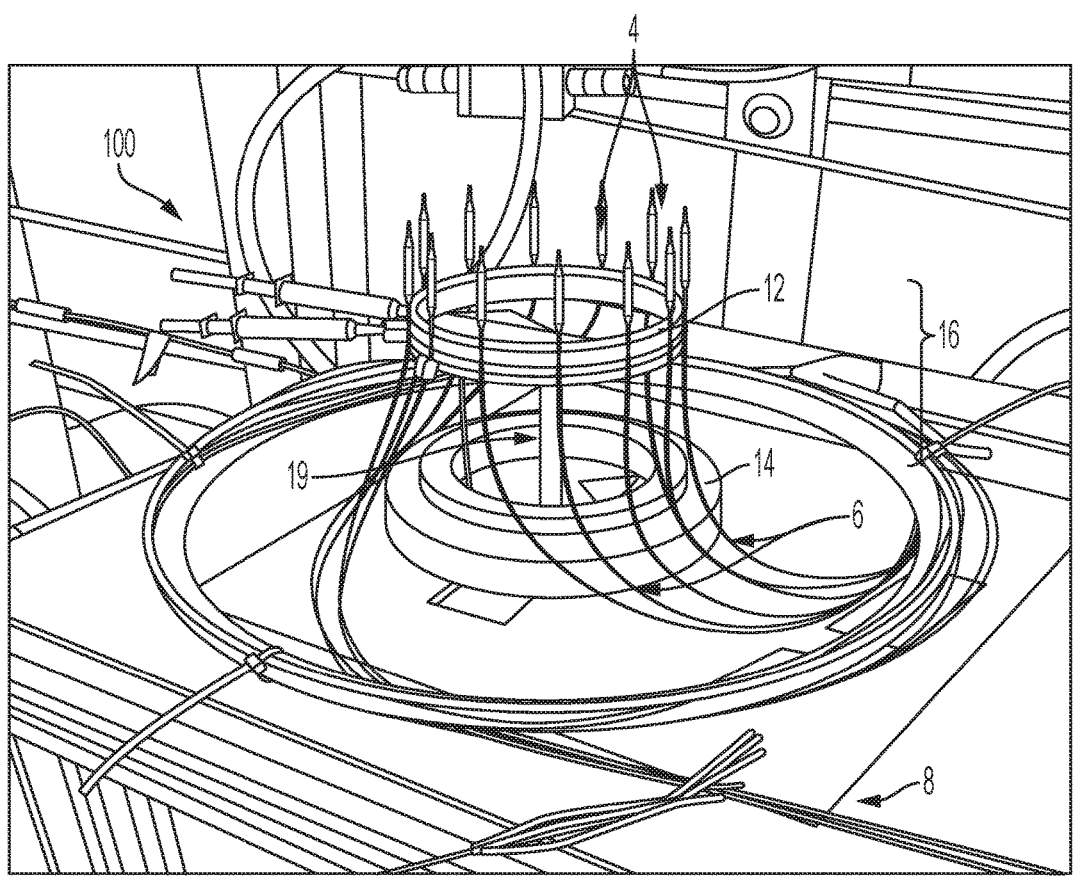
FIG. 3 shows a test configuration of system 100 for preparing e-RESS and e-STAT transferable coatings in accordance with the present invention

FIG. 3 shows a test configuration of system 100 for preparing e-RESS and e-STAT transferable coatings in accordance with the present invention. System 100 includes a balloon mounting assembly 16 for mounting and coating expandable medical devices including medical balloons 4. In the e-RESS coating process used in conjunction with the present invention, lower (base) staging ring 14, metal sheath (post) 19 surrounding e-RESS nozzle 18, and guide wires 8 are grounded. In the figure, medical balloons 4 are shown vertically mounted on upper staging ring 12 of mounting assembly 16. The upper ends of balloon catheters 6 are inserted in slots machined in the upper stage ring 12, providing vertical staging of balloons 4 for coating. Guide wires 8 (not shown) are enclosed within the balloons 4 within the internal catheter guide sleeves 6 (e.g., in a tube-within-a-balloon arrangement). At the top end of balloons 4, one end of guide wires 8 extends through sleeve 10 from inside the inner balloon 4, with the tip of the metal guide wire 8 retracted immediately (~1 mm) below the tip of balloon 4. Metal guide wires 8 extend a non-limiting distance of ~12 inches from the end of balloon 4 within catheter guide 6. Guide wires 8 protrude from the catheter guide 6, e.g., below base staging ring 14, which are then coupled to an electrical source 22 (e.g., a high voltage power supply). This arrangement allows preselected potentials or electrical grounding to be applied to each guide wire 8 that delivers an electric field through surfaces of each balloon 4 individually or collectively during deposition of coating particles. Retraction of the guide wire 8 into the balloon 4 prevents disruptive fields (i.e. coronal discharge) from forming at the exposed tip of wire 8 that can lead to poor quality depositions on the balloon 4 surface. Guide wires 8 in the instant embodiment, provide a convenient way to electrically connect the interior of the balloons 4 to the surface of the balloons 4, but the process is not intended to be limited to the use of catheter guide wires 8 as active electrodes. In one embodiment, base staging ring 14 is composed of a molded or machined engineering plastic (e.g., DELRIN®) to which a conductive metal (e.g., copper) grounding wire or ring (not shown) is positioned along the perimeter of lower staging ring 14, providing a common potential to each metal guide wire 8 during e-RESS coating of medical balloons 4 with e-RESS coating particles. In the instant embodiment, base ring 14 includes a loop for attaching guide wires 8 to grounding screws mounted next, or adjacent, to the conductive ring on base staging ring 14. The grounding ring further couples to a power source 22, e.g., using a clip mechanism or other attaching means, which permits guide wires 8 to be charged or grounded (when not charged) as required for preparation of specific coatings on the surface of medical balloons 4 described further herein. When charged, guide wires 8 provide a uniform field over the surface of balloon 4. In the test configuration, balloons 4 were inflated by connecting a 1 cm$^3$ (cc) syringe to a luer coupling (shown at left) located at the catheter 6 end of balloons 4 and fully depressing the syringe plunger, allowing the plunger to come back to an equilibrium position determined by the plunger friction in the syringe body, thereby providing a source of air that inflated each balloon 4. For commercial processing, a manifold of luer connections may be attached at the terminal ends of the catheters 6 and pumped to a pre-determined pressure such that each balloon 4 is pressurized equally for purposes of coating. A separate gas supply and pneumatics can be coupled for inflation of individual balloons 4 or simultaneous inflation of multiple balloons 4 during production. No limitations are intended.

Drug-Eluting Coatings

Composite coatings deposited to surfaces of expandable medical devices in conjunction with the invention using modified e-RESS and e-STAT processes can include various combinations of polymers and drugs in one or more coating layers that define the composite coating. Transferable deposits of the present invention prepared on the surfaces of expandable medical devices are preferably, but not exclusively, drug-eluting materials. The components of these composite coatings are subsequently transferred from the medical device to a specific location in a vessel (e.g., an artery) or other vascular location within a patient or host by activation or inflation of the balloons. Drugs and other therapeutic agents present in the various layers of the composite coating transferred are needed, thereby effecting treatment. Inclusion of a time-released drug or drugs in the transferred coating provides medical intervention or treatment at the delivery site over time (e.g., in a time-released fashion). The present invention further provides target delivery of a drug or drugs without need for long-term retention of the delivery device (i.e., the medical balloon or a stent) within the patient or host.

In one embodiment, the drug-eluting coating of transferrable material includes a drug that is dispersed in a matrix consisting of a biosorbable polymer that allows the drug to be deployed in a time-released fashion to a target location within the vascular system of the patient or host. In a preferred embodiment, the coating on the balloon that is completely or partially transferred to the vessel wall when deployed in the host vessel includes at least one layer that includes at least one drug. The coating may also include at least one biosorbable polymer (e.g., PLGA) in a single layer or in different layers. Tests conducted using medical-grade tubing as vessel surrogates and on test animals at conditions similar to those found in a human body have demonstrated that coating components collected on the surface of medical balloons using the above-described methods are successfully transferred to the inner vessel walls, forming a drug-eluting deposit within these specimens as detailed hereafter.

Polymer Coating Materials

In some embodiments, coating particles can include various materials selected from, e.g., polymers, drugs, biosorbable materials, bioactive proteins and peptides, as well as combinations of these materials. These materials find use in coatings that are applied to, e.g., medical devices (e.g., medical balloons) and medical implant devices (e.g., drug-eluting stents), but are not limited thereto. Choice for near-critical or supercritical fluid is based on the solubility of the selected solute(s) of interest, which is not limited.

Polymers used in conjunction with various embodiments include, but are not limited to, e.g., polylactoglycolic acid (PLGA); polyethylene vinyl acetate (PEVA); poly(butyl methacrylate) (PBMA); perfluorooctanoic acid (PFOA); tetrafluoroethylene (TFE); hexafluoropropylene (HFP); polylactic acid (PLA); polyglycolic acid (PGA); including combinations of these polymers. Other polymers include various mixtures of tetrafluoroethylene; hexafluoropropylene; and vinylidene fluoride (e.g., THV) at varying molecular ratios (e.g., 1:1:1).

Biosorbable polymers used in conjunction in some embodiments include, but are not limited to, e.g., polylactic acid (PLA); poly(DL-lactide-co-glycolide) (PLGA); poly (lactic-co-glycolic acid); polycaprolactone (poly(e-caprolactone)) (PCL); polyglycolide (PG) or (PGA); poly-3-hydroxybutyrate; LPLA poly(L-lactide); DLPLA poly(DL-lactide); PDO poly(dioxolane); PGA-TMC; 85/15 DLPLG poly(DL-lactide-co-glycolide); 75/25 DLPL; 65/35 DLPLG; 50/50 DLPLG; TMC poly(trimethylcarbonate); poly(CPP:SA); poly(1,3-bis-p-(carboxyphenoxy)propane-co-sebacic acid); and blends; combinations; homopolymers; condensation polymers; alternating; block; dendritic; crosslinked; and copolymers thereof.

Durable (biostable) polymers used in some embodiments include, but are not limited to, e.g., polyester; aliphatic polyester; polyanhydride; polyethylene; polyorthoester; polyphosphazene; polyurethane; polycarbonate urethane; aliphatic polycarbonate; silicone; a silicone-containing polymer; polyolefin; polyamide; polycaprolactam; polyamide; polyvinyl alcohol; acrylic polymer; acrylate; polystyrene; epoxy; polyethers; cellulosics; expanded polytetrafluoroethylene; phosphorylcholine; polyethylene-terephthalate; polymethylmethacrylate; poly(ethylmethacrylate/n-butylmethacrylate); parylene C; polyethylene-co-vinyl acetate; polyalkyl methacrylates; polyalkylene-co-vinyl acetate; polyalkylene; polyalkyl siloxanes; polyhydroxyalkanoate; polyfluoroalkoxyphosphazene; poly(styrene-b-isobutylene-b-styrene); poly-butyl methacrylate; poly-buta-diene; and blends; combinations; homopolymers; condensation polymers; alternating; block; dendritic; crosslinked; and copolymers thereof. Other polymers selected for use can include polymers to which drugs are chemically (e.g., ionically and/or covalently) attached or otherwise mixed, including, but not limited to, e.g., heparin-containing polymers (HCP).

Drugs/Drug Delivery

In various embodiments, time-released drugs are delivered to a wall of a vascular vessel (e.g., an artery) within a host or patient using a coating comprised of one or more coating layers. Coating layers can include various therapeutic agents in various combinations including, e.g., biosorbable polymers and drugs that are deposited onto the surface of, e.g., expandable polymer devices (e.g., a medical balloon). The expandable polymer device is subsequently transferred to, and deployed within the vascular system of a host or patient as detailed herein.

Drugs used in conjunction with various embodiments include, but are not limited to, e.g., antibiotics (e.g., Rapamycin [CAS No. 53123-88-9], LC Laboratories, Woburn, Mass., USA, anticoagulants (e.g., Heparin [CAS No. 9005-49-6]; antithrombotic agents (e.g., clopidogrel); antiplatelet drugs (e.g., aspirin); immunosuppressive drugs; antiproliferative drugs; chemotherapeutic agents (e.g., paclitaxel also known by the tradename TAXOL® [CAS No. 33069-62-4], Bristol-Myers Squibb Co., New York, N.Y., USA) and/or a pro-drug, a derivative, an analog, a hydrate, an ester, and/or a salt thereof). Examples of antibiotics include, but are not limited to, e.g., amikacin, amoxicillin, gentamicin, kanamycin, neomycin, netilmicin, paromomycin, tobramycin, geldanamycin, herbimycin, carbacephem (loracarbef), ertapenem, doripenem, imipenem, cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, clarithromycin, clavulanic acid, clindamycin, teicoplanin, azithromycin, dirithromycin, erythromycin, troleandomycin, telithromycin, aztreonam, ampicillin, azlocillin, bacampicillin, carbenicillin, cloxacillin, dicloxacillin, flucloxacillin, mezlocillin, meticillin, nafcillin, norfloxacin, oxacillin, penicillin-G, penicillin-V, piperacillin, pvampicillin, pivmecillinam, ticarcillin, bacitracin, colistin, polymyxin-B, ciprofloxacin, enoxacin, gatifloxacin, levofloxacin, lomefloxacin, moxifloxacin, o floxacin, trovafloxacin, grepafloxacin, sparfloxacin, afenide, prontosil, sulfacetamide, sulfamethizole, sulfanilimide, sulfamethoxazole, sulfisoxazole, trimethoprim, trimethoprim-sulfamethoxazole, demeclocycline, doxycycline, oxytetracycline, tetracycline, arsphenamine, chloramphenicol, lincomycin, ethambutol, fosfomycin, furazolidone, isoniazid, linezolid, mupirocin, nitrofurantoin, platensimycin, pyrazinamide, quinupristin/dalfopristin, rifampin, thiamphenicol, rifampicin, minocycline, sultamicillin, sulbactam, sulphonamides, mitomycin, spectinomycin, spiramycin, roxithromycin, and meropenem. Antibiotics can also be grouped into classes of related drugs, for example, aminoglycosides (e.g., amikacin, gentamicin, kanamycin, neomycin, netilmicin, paromomycin, streptomycin, tobramycin), ansamycins (e.g., geldanamycin, herbimycin), carbacephem (loracarbef) carbapenems (e.g., ertapenem, doripenem, imipenem, meropenem), first generation cephalosporins (e.g., cefadroxil, cefazolin, cefalotin, cefalexin), second generation cephalosporins (e.g., cefaclor, cefamandole, cefoxitin, cefprozil, cefuroxime), third generation cephalosporins (e.g., cefixime, cefdinir, cefditoren, cefoperazone, cefotaxime, cefpodoxime, ceftazidime, ceftibuten, ceftizoxime, ceftriaxone), fourth generation cephalosporins (e.g., cefepime), fifth generation cephalosporins (e.g., ceftobiprole), glycopeptides (e.g., teicoplanin, vancomycin), macrolides (e.g., azithromycin, clarithromycin, dirithromycin, erythromycin, roxithromycin, troleandomycin, telithromycin, spectinomycin), monobactams (e.g., aztreonam), penicillins (e.g., amoxicillin, ampicillin, azlocillin, bacampicillin, carbenicillin, cloxacillin, dicloxacillin, flucloxacillin, mezlocillin, meticillin, nafcillin, oxacillin, penicillins-G and -V, piperacillin, pvampicillin, pivmecillinam, ticarcillin), polypeptides (e.g., bacitracin, colistin, polymyxin-B), quinolones (e.g., ciprofloxacin, enoxacin, gatifloxacin, levofloxacin, lomefloxacin, moxifloxacin, norfloxacin, ofloxacin, trovafloxacin, grepafloxacin, sparfloxacin, trovafloxacin), sulfonamides (e.g., afenide, prontosil, sulfacetamide, sulfamethizole, sulfanilimide, sulfasalazine, sulfamethoxazole, sulfisoxazole, trimethoprim, trimethoprim-sulfamethoxazole), tetracyclines (e.g., demeclocycline, doxycycline, minocycline, oxytetracycline, tetracycline).

Drugs used in some embodiments described herein include, but are not limited to, e.g., immunosuppressive drugs such as a macrolide immunosuppressive drug, which may comprise one or more of: rapamycin; biolimus (biolimus A9); 40-O-(2-Hydroxyethyl)rapamycin (everolimus); 40-O-Benzyl-rapamycin; 40-O-(4'-Hydroxymethyl)benzyl-rapamycin; 40-O-[4'-(1,2-Dihydroxyethyl)]benzyl-rapamycin; 40-O-Allyl-rapamycin; 40-O-[3'-(2,2-Dimethyl-1,3-dioxolan-4(S)-yl)-prop-2'-en-1'-yl]-rapamycin; (2':E,4'S)-40-O-(4',5'-Dihydroxypent-2'-en-1'-yl)-rapamycin; 40-O-(2-Hydroxy)ethoxycar-bonylmethyl-rapamycin; 40-O-(3-Hydroxy)propyl-rapamycin; 40-O-(6-Hydroxy)hexyl-rapamycin; 40-O-[2-(2-Hydroxy)ethoxy]ethyl-rapamycin; 40-O-[(3S)-2,2-Dimethyldioxolan-3-yl]methyl-rapamycin; 40-O-[(2S)-2,3-Dihydroxyprop-1-yl]-rapamycin; 40-O-(2-Acetoxy)ethyl-rapamycin; 40-O-(2-Nicotinoyloxy)ethyl-rapamycin; 40-O-[2-(N-Morpholino)acetoxy]ethyl-rapamycin; 40-O-(2-N-Imidazolylacetoxy)ethyl-rapamycin; 40-O-[2-(N-Methyl-N'-piperazinyl)acetoxy]ethyl-rapamycin; 39-O-Desmethyl-39-40-O,O-ethylene-rapamycin; (26R)-26-Dihydro-40-O-(2-hydroxy)ethyl-rapamycin; 28-O-Methyl-rapamycin; 40-O-(2-Aminoethyl)-rapamycin; 40-O-(2-Acetaminoethyl)-rapamycin; 40-O-(2-Nicotinamidoethyl)-rapamycin; 40-O-(2-(N-Methyl-imidazo-2'-ylcarbethoxamido)ethyl)-rapamycin; 40-O-(2-Ethoxycarbonylaminoethyl)-rapamycin; 40-O-(2-Tolylsulfonamidoethyl)-rapamycin; 40-O-[2-(4',5'-Dicarboethoxy-1',2',3'-triazol-1'-yl)-ethyl]-rapamycin; 42-Epi-(tetrazolyl)rapamycin (tacrolimus); 42-[3-hydroxy-2-(hydroxymethyl)-2-methylpropanoate]rapamycin (temsirolimus); (42S)-42-Deoxy-42-(1H-tetrazol-1-yl)-rapamycin (zotarolimus); and salts, derivatives, isomers, racemates, diastereoisomers, pro-drugs, hydrates, esters, or analogs thereof.

Drugs used in various embodiments described further herein include, but are not limited to, e.g., Acarbose; acetylsalicylic acid; acyclovir; allopurinol; alprostadil; prostaglandins; amantadine; ambroxol; amlodipine; S-amino salicylic acid; amitriptyline; atenolol; azathioprine; balsalazide; beclomethasone; betahistine; bezafibrate; diazepam and diazepam derivatives; budesonide; bufexamac; buprenorphine; butizine; methadone; calcium salts; potassium salts; magnesium salts; candesartan; carbamazepine; captopril; cetirizine; chenodeoxycholic acid; theophylline and theophylline derivatives; trypsins; cimetidine; clobutinol; clonidine; cotrimoxazole; codeine; caffeine; vitamin D and derivatives of vitamin D; colestyramine; cromoglicic acid; coumarin and coumarin derivatives; cysteine; ciclosporin; cyproterone; cytabarine; dapiprazole; desogestrel; desonide; dihydralazine; diltiazem; ergot alkaloids; dimenhydrinate; dimethyl sulphoxide; dimeticone; domperidone and domperidan derivatives; dopamine; doxazocin; doxylamine; benzodiazepines; diclofenac; desipramine; econazole; ACE inhibitors; enalapril; ephedrine; epinephrine; epoetin and epoetin derivatives; morphinans; calcium antagonists; modafinil; orlistat; peptide antibiotics; phenytoin; riluzoles; risedronate; sildenafil; topiramate; estrogen; progestogen and progestogen derivatives; testosterone derivatives; androgen and androgen derivatives; ethenzamide; etofenamate; etofibrate; fenofibrate; etofylline; famciclovir; famotidine; felodipine; fentanyl; fenticonazole; gyrase inhibitors; fluconazole; fluarizine; fluoxetine; flurbiprofen; ibuprofen; fluvastatin; follitropin; formoterol; fosfomicin; furosemide; fusidic acid; gallopamil; ganciclovir; gemfibrozil; ginkgo; Saint John's wort; glibenclamide; urea derivatives as oral antidiabetics; glucagon; glucosamine and glucosamine derivatives; glutathione; glycerol and glycerol derivatives; hypothalamus hormones; guanethidine; halofantrine; haloperidol; heparin (and derivatives); hyaluronic acid; hydralazine; hydrochlorothiazide (and derivatives); salicylates; hydroxyzine; imipramine; indometacin; indoramine; insulin; iodine and iodine derivatives; isoconazole; isoprenaline; glucitol and glucitol derivatives; itraconazole; ketoprofen; ketotifen; lacidipine; lansoprazole; levodopa; levomethadone; thyroid hormones; lipoic acid (and derivatives); lisinopril; lisuride; lofepramine; loperamide; loratadine; maprotiline; mebendazole; mebeverine; meclozine; mefenamic acid; mefloquine; meloxicam; mepindolol; meprobamate; mesalazine; mesuximide; metamizole; metformin; methylphenidate; metixene; metoprolol; metronidazole; mianserin; miconazole; minoxidil; misoprostol; mizolastine; moexipril; morphine and morphine derivatives; evening primrose; nalbuphine; naloxone; tilidine; naproxen; narcotine; natamycin; neostigmine; nicergoline; nicotinamide; nifedipine; niflumic acid; nimodipine; nimorazole; nimustine; nisoldipine; adrenaline and adrenaline derivatives; novamine sulfone; noscapine; nystatin; o lanzapine; olsalazine; omeprazole; omoconazole; oxaceprol; oxiconazole; oxymetazoline; pantoprazole; paracetamol (acetaminophen); paroxetine; penciclovir; pentazocine; pentifylline; pentoxifylline; perphenazine; pethidine; plant extracts; phenazone; pheniramine; barbituric acid derivatives; phenylbutazone; pimozide; pindolol; piperazine; piracetam; pirenzepine; piribedil; piroxicam; pramipexole; pravastatin; prazosin; procaine; promazine; propiverine; propranolol; propyphenazone; protionamide; proxyphylline; quetiapine; quinapril; quinaprilat; ramipril; ranitidine; reproterol; reserpine; ribavirin; risperidone; ritonavir; ropinirole; roxatidine; rus- cogenin; rutoside (and derivatives); sabadilla; salbutamol; salmeterol; scopolamine; selegiline; sertaconazole; sertindole; sertralion; silicates; simvastatin; sitosterol; sotalol; spaglumic acid; spirapril; spironolactone; stavudine; streptomycin; sucralfate; sufentanil; sulfasalazine; sulpiride; sultiam; sumatriptan; suxamethonium chloride; tacrine; tacrolimus; taliolol; taurolidine; temazepam; tenoxicam; terazosin; terbinafine; terbutaline; terfenadine; terlipressin; tertatolol; teryzo line; theobromine; thiamazole; phenothiazines; tiagabine; tiapride; propionic acid derivatives; ticlopidine; timolol; tinidazole; tioconazole; tioguanine; tioxolone; tiropramide; tizanidine; tolazoline; tolbutamide; tolcapone; tolnaftate; tolperisone; topotecan; torasemide; tramadol; tramazoline; trandolapril; tranylcypromine; trapidil; trazodone; triamcinolone derivatives; triamterene; trifluperidol; trifluridine; trimipramine; tripelennamine; triprolidine; trifosfamide; tromantadine; trometamol; tropalpin; troxerutine; tulobuterol; tyramine; tyrothricin; urapidil; valaciclovir; valproic acid; vancomycin; vecuronium chloride; Viagra; venlafaxine; verapamil; vidarabine; vigabatrin; viloazine; vincamine; vinpocetine; viquidil; warfarin; xantinol nicotinate; xipamide; zafirlukast; zalcitabine; zidovudine; zolmitriptan; zolpidem; zoplicone; zotipine; amphotericin B; caspo fungin; voriconazole; resveratrol; PARP-1 inhibitors (including imidazoquinolinone; imidazpyridine; and isoquinolindione); tissue plasminogen activator (tPA); melagatran; lanoteplase; reteplase; staphylokinase; streptokinase; tenecteplase; urokinase; abciximab (ReoPro); eptifibatide; tirofiban; prasugrel; clopidogrel; dipyridamole; cilostazol; VEGF; heparan sulfate; chondroitin sulfate; elongated "RGD" peptide binding domain; CD34 antibodies; cerivastatin; etorvastatin; losartan; valartan; erythropoietin; rosiglitazone; pioglitazone; mutant protein Apo A1 Milano; adiponectin; (NOS) gene therapy; glucagon-like peptide 1; atorvastatin; and atrial natriuretic peptide (ANP); lidocaine; tetracaine; dibucaine; hyssop; ginger; turmeric; *Arnica montana*; helenalin; cannabichromene; rofecoxib; hyaluronidase; and salts, derivatives, isomers, racemates, diastereoisomers, prodrugs, hydrates, esters, or analogs thereof.

Anti-thrombotic Agents

Anti-thrombotic agents (e.g., clopidogrel) are also contemplated for use in the methods and devices described herein. Use of anti-platelet drugs (e.g., aspirin), for example, to prevent platelet binding to exposed collagen, is contemplated for anti-restenotic or anti-thrombotic therapy. Anti-platelet agents include "GpIIb/IIIa inhibitors" (e.g., abciximab, eptifibatide, tirofiban, RheoPro) and "ADP receptor blockers" (prasugrel, clopidogrel, ticlopidine). Particularly useful for local therapy are dipyridamole, which has local vascular effects that improve endothelial function (e.g., by causing local release oft-PA, that will break up clots or prevent clot formation) and reduce the likelihood of platelets and inflammatory cells binding to damaged endothelium, and cAMP phosphodiesterase inhibitors, e.g., cilostazol, that could bind to receptors on either injured endothelial cells or bound and injured platelets to prevent further platelet binding.

Chemotherapeutic Agents

Chemotherapeutic agents may also be used. Examples of chemotherapeutic agents include, but are not limited to, e.g., angiostatin; DNA topoisomerase; endostatin; genistein; ornithine decarboxylase inhibitors; chlormethine; melphalan; pipobroman; triethylene-melamine; triethylenethiophosphoramine; busulfan; carmustine (BCNU); streptozocin; 6-mercaptopurine; 6-thioguanine; deoxyco-formycin; IFN-α; 17α-ethinylestradiol; diethylstilbestrol; testosterone; prednisone; fluoxymesterone; dromostanolone propionate; testolactone; megestrolacetate; methylprednisolone; methyltestosterone; prednisolone; triamcinolone; chlorotrianisene; hydroxyprogesterone; estramustine; medroxyprogesteroneacetate; flutamide; zoladex; mitotane; hexamethylmelamine; indolyl-3-glyoxylic acid derivatives; (e.g., indibulin); doxorubicin and idarubicin; plicamycin (mithramycin) and mitomycin; mechlorethamine; cyclophosphamide analogs; trazenes-dacarbazinine (DTIC); pentostatin and 2-chlorodeoxyadenosine; letrozole; camptothecin (and derivatives); navelbine; erlotinib; capecitabine; acivicin; acodazole hydrochloride; acronine; adozelesin; aldesleukin; ambomycin; ametantrone acetate; anthramycin; asperlin; azacitidine; azetepa; azotomycin; batimastat; benzodepa; bisnafide; bisnafide dimesylate; bizelesin; bropirimine; cactinomycin; calusterone; carbetimer; carubicin hydrochloride; carzelesin; cedefingol; celecoxib (COX-2 inhibitor); cirolemycin; crisnatol mesylate; decitabine; dexormaplatin; dezaguanine mesylate; diaziquone; duazomycin; edatrexate; eflornithine; elsamitrucin; enloplatin; enpromate; epipropidine; erbulozole; etanidazole; etoprine; flurocitabine; fosquidone; lometrexol; losoxantrone hydrochloride; masoprocol; maytansine; megestrol acetate; melengestrol acetate; metoprine; meturedepa; mitindomide; mitocarcin; mitocromin; mitogillin; mitomalcin; mitosper; mycophenolic acid; nocodazole; nogalamycin; ormaplatin; oxisuran; pegaspargase; peliomycin; pentamustine; perfosfamide; piposulfan; plomestane; porfimer sodium; porfiromycin; puromycin; pyrazofurin; riboprine; safingol; simtrazene; sparfosate sodium; spiromustine; spiroplatin; streptonigrin; sulofenur; tecogalan sodium; taxotere; tegafur; teloxantrone hydrochloride; temoporfin; thiamiprine; tirapazamine; trestolone acetate; triciribine phosphate; trimetrexate glucuronate; tubulozole hydrochloride; uracil mustard; uredepa; verteporfin; vinepidine sulfate; vinglycinate sulfate; vinleurosine sulfate; vinorelbine tartrate; vinrosidine sulfate; zeniplatin; zinostatin; 20-epi-1,25 dihydroxyvitamin-D3; 5-ethynyluracil; acylfulvene; adecypenol; ALL-TK antagonists; ambamustine; amidox; amifostine; aminolevulinic acid; amrubicin; anagrelide; andrographolide; antagonist-D; antagonist-G; antarelix; anti-dorsalizing morphogenetic protein-1; antiandrogen; antiestrogen; estrogen agonist; apurinic acid; ara-CDP-DL-PTBA; arginine deaminase; asulacrine; atamestane; atrimustine; axinastatin-1; axinastatin-2; axinastatin-3; azasetron; azatoxin; azatyrosine; baccatin III derivatives; balanol; BCR/ABL antagonists; benzochlorins; benzoylstaurosporine; beta lactam derivatives; beta-alethine; betaclamycin-B; betulinic acid; bFGF inhibitor; bisaziridinylspermine; bistratene-A; breflate; buthionine sulfoximine; calcipotriol; calphostin-C; carboxamide-amino-triazole; carboxyamidotriazole; CaRest M3; CARN 700; cartilage derived inhibitor; casein kinase inhibitors (ICOS); castanospermine; cecropin B; cetrorelix; chloroquinoxaline sulfonamide; cicaprost; cis-porphyrin; clomifene analogues; clotrimazole; collismycin-A; collismycin-B; combretastatin-A4; combretastatin analogue; conagenin; crambescidin-816; cryptophycin-8; cryptophycin-A derivatives; curacin-A; cyclopentanthraquinones; cycloplatam; cypemycin; cytolytic factor; cytostatin; dacliximab; dehydrodidemnin B; dexamethasone; dexifosfamide; dexrazoxane; dexverapamil; didemnin-B; didox; diethylnorspermine; dihydro-5-azacytidine; dihydrotaxol; docosanol; dolasetron; dronabinol; duocarmycin-SA; ebselen; ecomustine; edelfosine; edrecolomab; elemene; emitefur; estramustine analogue; filgrastim; flavopiridol; flezelastine; fluasterone; fluorodaunorunicin hydrochloride; forfenimex; gadolinium texaphyrin; galocitabine; gelatinase inhibitors; glutathione inhibitors; hepsulfam; heregulin; hexamethylene bisacetamide; hypericin; ibandronic acid; idramantone; ilomastat; imatinib (e.g., Gleevec); imiquimod; immunostimulant peptides; insulin-like growth factor-1 receptor inhibitor; interferon agonists; interferons; interleukins; iobenguane; iododoxorubicin; ipomeanol; iroplact; irsogladine; isobengazole; isohomohalicondrin-B; itasetron; jasplakinolide; kahalalide-F; lamellarin-N triacetate; leinamycin; lenograstim; lentinan sulfate; leptolstatin; leukemia inhibiting factor; leukocyte alpha interferon; leuprolide+estrogen+progesterone; linear polyamine analogue; lipophilic disaccharide peptide; lipophilic platinum compounds; lissoclinamide-7; lobaplatin; lombricine; loxoribine; lurtotecan; lutetium texaphyrin; lysofylline; lytic peptides; maitansine; mannostatin-A; marimastat; maspin; matrilysin inhibitors; matrix metalloproteinase inhibitors; meterelin; methioninase; metoclopramide; MIF inhibitor; mifepristone; miltefosine; mirimostim; mitoguazone; mitotoxin fibroblast growth factor-saporin; mofarotene; molgramostim; Erbitux; human chorionic gonadotrophin; monophosphoryl lipid A+myobacterium cell wall sk; mustard anticancer agent; mycaperoxide-B, mycobacterial cell wall extract, myriaporone, N-acetyldinaline, N-substituted benzamides, nagrestip, naloxone+pentazocine, napavin, naphterpin, nartograstim, nedaplatin, nemorubicin, neridronic acid, nisamycin, nitric oxide modulators, nitroxide antioxidant, nitrullyn, oblimersen (Genasense), O6-benzylguanine, okicenone, onapristone, ondansetron, oracin, oral cytokine inducer, paclitaxel analogues and derivatives, palauamine, palmitoylrhizoxin, pamidronic acid, panaxytriol, panomifene, parabactin, peldesine, pentosan polysulfate sodium, pentrozole, perflubron, perillyl alcohol, phenazinomycin, phenylacetate, phosphatase inhibitors, picibanil, pilocarpine hydrochloride, placetin-A, placetin-B, plasminogen activator inhibitor, platinum complex, platinum compounds, platinum-triamine complex, propyl bis-acridone, prostaglandin-J2, proteasome inhibitors, protein A-based immune modulator, protein kinase-C inhibitors, microalgal, pyrazoloacridine, pyridoxylated hemoglobin polyoxyethylene conjugate, raf antagonists, raltitrexed, ramosetron, ras farnesyl protein transferase inhibitors, ras-GAP inhibitor, retelliptine demethylated, rhenium Re-186 etidronate, ribozymes, RII retinamide, rohitukine, romurtide, roquinimex, rubiginone-B1, ruboxyl, saintopin, SarCNU, sarcophytol A, sargramostim, Sdi-1 mimetics, senescence derived inhibitor-1, signal transduction inhibitors, sizofiran, sobuzoxane, sodium borocaptate, solverol, somatomedin binding protein, sonermin, sparfosic acid, spicamycin-D, splenopentin, spongistatin-1, squalamine, stipiamide, stromelysin inhibitors, sulfinosine, superactive vasoactive intestinal peptide antagonist, suradista, suramin, swainsonine, tallimustine, tazarotene, tellurapyrylium, telomerase inhibitors, tetrachlorodecaoxide, tetrazomine, thiocoraline, thrombopoietin, thrombopoietin mimetic, thymalfasin, thymopoietin receptor agonist, thymotrinan, thyroid stimulating hormone, tin ethyl etiopurpurin, titanocene bichloride, topsentin, translation inhibitors, tretinoin, triacetyluridine, tropisetron, turosteride, ubenimex, urogenital sinus-derived growth inhibitory factor, variolin-B, velaresol, veramine, verdins, vinxaltine, vitaxin, zanoterone, zilascorb, zinostatin stimalamer, acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazaribine, floxuridine, fludarabine, fludarabine phosphate, N-(2'-furanidyl)-5-fluorouracil, Daiichi Seiyaku FO-152, 5-FU-fibrinogen, isopropyl pyrrolizine, Lilly LY-188011, Lilly LY-264618, methobenzaprim, methotrexate, Wellcome MZPES, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate, Takeda TAC-788, thioguanine, tiazofurin, Erbamont TIF, trimetrexate, tyrosine kinase inhibitors, tyrosine protein kinase inhibitors, Taiho UFT, uricytin, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Chugai DWA-2114R, ITI E09, elmustine, Erbamont FCE-24517, estramustine phosphate sodium, etoposide phosphate, fotemustine, Unimed G-6-M, Chinoin GYKI-17230, hepsul-fam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide, teroxirone, tetraplatin and trimelamol, Taiho 4181-A, aclarubicin, actinomycin-D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitomycin analogues, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024, zorubicin, 5-fluorouracil (5-FU), the peroxidate oxidation product of inosine, adenosine, or cytidine with methanol or ethanol, cytosine arabinoside (also referred to as Cytarabin, araC, and Cytosar), 5-Azacytidine, 2-Fluoroadenosine-5'-phosphate (Fludara, also referred to as FaraA), 2-Chlorodeoxyadenosine, Abarelix, Abbott A-84861, Abiraterone acetate, Aminoglutethimide, Asta Medica AN-207, Antide, Chugai AG-041R, Avorelin, aseranox, Sensus B2036-PEG, buserelin, BTG CB-7598, BTG CB-7630, Casodex, cetrolix, clastroban, clodronate disodium, Cosudex, Rotta Research CR-1505, cytadren, crinone, deslorelin, droloxifene, dutasteride, Elimina, Laval University EM-800, Laval University EM-652, epitiostanol, epristeride, Mediolanum EP-23904, EntreMed 2-ME, exemestane, fadrozole, finasteride, formestane, Pharmacia & Upjohn FCE-24304, ganirelix, goserelin, Shire gonadorelin agonist, Glaxo Wellcome GW-5638, Hoechst Marion Roussel Hoe-766, NCI hCG, idoxifene, isocordoin, Zeneca ICI-182780, Zeneca ICI-118630, Tulane University J015X, Schering Ag J96, ketanserin, lanreotide, Milkhaus LDI-200, letrozol, leuprolide, leuprorelin, liarozole, lisuride hydrogen maleate, loxiglumide, mepitiostane, Ligand Pharmaceuticals LG-1127, LG-1447, LG-2293, LG-2527, LG-2716, Bone Care International LR-103, Lilly LY-326315, Lilly LY-353381-HCl, Lilly LY-326391, Lilly LY-353381, Lilly LY-357489, miproxifene phosphate, Orion Pharma MPV-2213ad, Tulane University MZ-4-71, nafarelin, nilutamide, Snow Brand NKS01, Azko Nobel ORG-31710, Azko Nobel ORG-31806, orimeten, orimetene, orimetine, ormeloxifene, osaterone, Smithkline Beecham SKB-105657, Tokyo University OS W-1, Peptech PTL-03001, Pharmacia & Upjohn PNU-156765, quinagolide, ramorelix, Raloxifene, statin, sandostatin LAR, Shionogi S-10364, Novartis SMT-487, somavert, somatostatin, tamoxifen, tamoxifen methiodide, teverelix, toremifene, triptorelin, TT-232, vapreotide, vorozole, Yamanouchi YM-116, Yamanouchi YM-511, Yamanouchi YM-55208, Yamanouchi YM-53789, Schering AG ZK-1911703, Schering AG ZK-230211, and Zeneca ZD-182780, alpha-carotene, alpha-difluoromethyl-arginine, acitretin, Biotec AD-5, Kyorin AHC-52, alstonine, amonafide, amphethinile, amsacrine, Angiostat, ankinomycin, antineoplaston-A10, antineoplaston-A2, antineoplaston-A3, antineoplaston-A5, antineoplaston-AS2-1, Henkel-APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, datelliptinium, DFMO, didemnin-B, dihaematoporphyrin ether, dihydrolenperone dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin, Cell Pathways Exisulind (sulindac sulphone or CP-246), fenretinide, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron, Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide-D, piroxantrone, polyhaematoporphyrin, polypreic acid, Efamol porphyrin, probimane, procarbazine, proglumide, Invitron protease nexin I, Tobishi RA-700, razoxane, retinoids, R-flurbiprofen (Encore Pharmaceuticals), Sandostatin, Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, selenium (selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine, vinblastine sulfate, vincristine, vincristine sulfate, vindesine, vindesine sulfate, vinestramide, vinorelbine, vintriptol, vinzolidine, withanolides, Yamanouchi YM-534, Zileuton, ursodeoxycholic acid, Zanosar. Drug choices are not intended to be limited. For example, coatings on medical devices can include drugs used in time-release drug applications. Proteins may be coated according to these methods and coatings described herein may comprise proteins. Peptides may be coated according to these methods and coatings described herein may comprise peptides.

Releasing Agents

In some embodiments, coating particles can include releasing agents, which may include low-energy releasing agents (also called low-energy release agents). Releasing agents may also be called a "release agent." These materials find use in coatings that are applied to, e.g., medical devices (e.g., medical balloons) and medical implant devices (e.g., drug-eluting stents), but are not limited thereto. Choice for near-critical or supercritical fluid is based on the solubility of the selected solute(s) of interest, which is not limited.

A release agent may comprise: hydrophilic or hydrophobic chemicals or polymers that lower the interfacial energy between the surface of the medical device and the coating layers, water soluble chemicals or polymers that dissolve to eliminate adhesion between coatings layers and the medical device surface, brittle or friable coatings that lose mechanical cohesion upon, Polyethylene glycols (PEG), Hydrogels, Polyesters, Polyacrylates, Polysaccharides, Silicones, Silanes, Tocopherol, Glycerin, Sucrose, Cellulose, and Shellac.

A low-energy releasing agents may be a subset of the larger set of releasing agents. A releasing agent that is "low-energy" may be defined as a releasing agent with surface energy of less than 35 dynes/cm or agents onto which a drop of water would experience a contact angle of greater than 90 degrees. Examples of low-energy releasing agents include (but are not limited to): Polyvinyl alcohols (PVA), Ethylene vinyl acetates (EVA), Polyolefins, Fluorosilanes, Fluoroacrylates, Fluorohydrocarbons, Paraffin, and Long chain hydrocarbons.

Adhesive Agents

In some embodiments, coating particles can include adhesive agents that serve to affix the balloon coating to a receiving surface when the surface is contacted. Adhesive agents may comprise any one or more of the following: agents with cationic moieties that assist in cellular adhesion/uptake, shattering agents that penetrate tissue surface and promote adhesion through mechanical entanglement, viscous polymeric agents, and cationic polyamino acids. Cationic polyamino acids include, but are not limited to: polyarginine, polylysine, polyhistidine, and polyethyleneimine (PEI). Adhesive agents may comprise any one or more of the following: 3,4-dihydroxy-L-phenylalanine (dopa), (as in active component in mussel adhesive), laminins, and cationic surfactant molecules. Cationic surfactant molecules include, but are not limited to: didodecyldimethylammonium bromide (DMAB), ethylhexadecyldimethylammonium bromide, do decyltrimethyl ammonium bromide, tetradodecylammonium bromide, dimethylditetradecylammonium bromide, tetrabutylammonium iodide, DEAE-dextran hydrochloride, and hexadimethrine bromide.

e-RESS Generated Coating Layers

Figure 4:
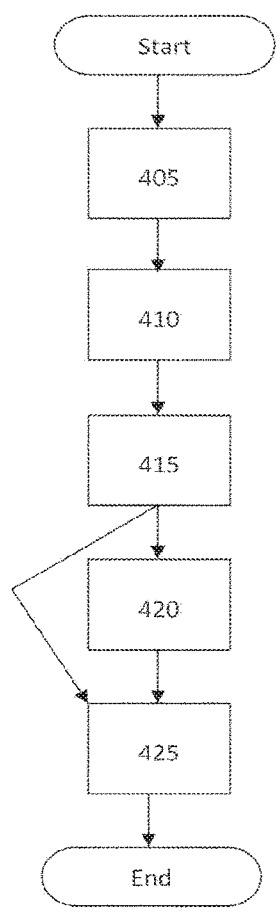
FIG. 4 presents exemplary process steps for delivering e-RESS coating layers as a component of transferable coatings formed in accordance with an embodiment of the invention.

FIG. 4 presents exemplary process steps for generating e-RESS coating layers on expandable medical balloons that deliver transferable, drug-eluting deposits at target locations within a host or patient, according to an embodiment of the invention. In a first step (405), a preselected solvent is intermixed with at least one coating material at a preselected pressure or temperature to form a supercritical solution. Next (410), the selected coating material is discharged from the supercritical solution through a restrictor nozzle (FIG. 1) as a RESS plume to form e-RESS charged coating particles at a preselected pressure and temperature. Next (415), the e-RESS generated charged coating particles are delivered to the surface of the balloon to form a coating layer containing the charged coating particles. In some embodiments, the particles are electrostatically attracted to the surface of the balloon either with or without the addition of an actively induced electrostatic field. In an optional step (420), the coating layer containing the charged coating particles is sintered to form a stable RESS film layer, e.g., on the surface of the balloon. Next (425), form one or more coating layers on the surface of the balloon using the e-RESS process.

e-STAT Generated Coating Layers

Figure 5:
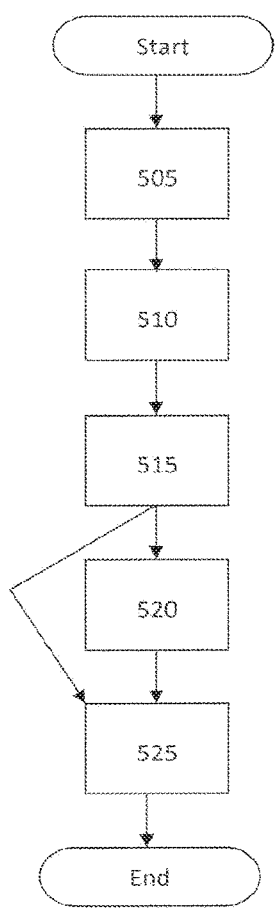
FIG. 5 presents exemplary process steps for delivering e-STAT coating layers as a component of transferable coatings formed in accordance with an embodiment of the invention.

FIG. 5 presents exemplary process steps for generating e-STAT coating layers as a component of drug-eluting coatings formed in accordance with an embodiment of the invention. First (505), a potential is applied to the conductive element located within the expandable medical balloon to generate a selected potential on the surface of the balloon as described herein. A potential of −15 kV is typical. However, potentials are not intended to be limited thereto. Next (510), a preselected coating material is discharged as a plume of dry charged (e-STAT) coating particles in an inert discharge gas absent a solvent at a preselected pressure and temperature. Next (515), the dry charged coating particles containing the preselected coating material are electrostatically attracted to the surface of the balloon to form a dry coating layer on the surface of the balloon. In some embodiments, the electrostatic attraction between the particles and the balloon surface is performed with or without the addition of an actively induced electrostatic field. In an optional step (520), the coating layer containing the charged coating particles is sintered to form a stable e-STAT film layer on the surface of the balloon or to stabilize the e-STAT particles by fusing them to a previously deposited polymer layer. Next (525), the e-STAT process is repeated as necessary to form one or more coating layers on the surface of the balloon.

Combined e-RESS/e-STAT Generated Coating Layers

Figure 6:
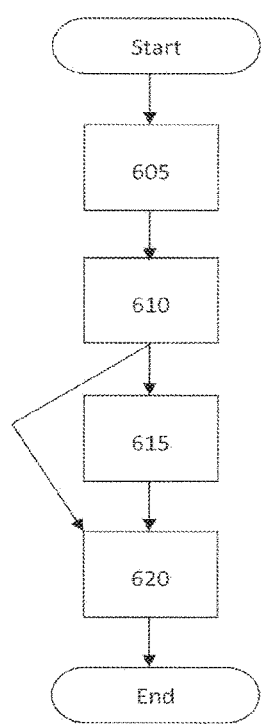
FIG. 6 presents exemplary process steps for delivering combined e-RESS/e-STAT coating layers as a component of transferable coatings formed in accordance with an embodiment of the invention.

FIG. 6 presents exemplary process steps for generating combined e-RESS/e-STAT coating layers as a component of drug-eluting coatings formed in accordance with an embodiment of the invention. First (605), e-RESS generated charged coating particles and/or e-STAT generated charged coating particles containing a preselected coating material are discharged in respective plumes at a preselected pressure and temperature. In some embodiments, the plumes containing the e-RESS and/or e-STAT generated charged coating particles can be discharged as separately in respective plumes or simultaneously in combined plumes in any order. No limitations are intended. Next (610), the e-RESS and/or e-STAT charged coating particles containing the preselected coating material are delivered to the surface of the balloon to form one or more coating layers containing the charged coating particles on the surface of the balloon. In some embodiments, the particles are electrostatically attracted to the surface of the balloon either with or without the addition of an actively induced electrostatic field. In an optional step (615), the e-RESS and/or e-STAT coating layers containing the charged coating particles are sintered to form stable coating layers on the surface of the balloon. Next (620), one or more e-RESS and/or e-STAT coating layers are formed on the surface of the balloon using e-RESS and/or e-STAT processes performed individually, serially, or simultaneously.

Delivery of Coatings that Form Drug-Eluting Deposits

The transferable material or "portion of the coating" is delivered from the surface of the medical balloon to the target site within the vascular system of the patient or host by expanding the medical balloon within the receiving vessel (e.g., an artery or other vessel) at the location where the therapeutic drug or other therapeutic agent is needed. This process transfers the drug-eluting composite (or "material") to the host vessel (e.g., artery or vein) providing treatment or medical intervention in the host or patient. In exemplary tests, coatings comprised of one or more layers including a biosorbable polymer and drug were successfully deployed within the vascular system of a host or patient. Delivery and placement of all or portions of a cylindrical coating consisting of a therapeutic drug (e.g., rapamycin) encapsulated in a biosorbable polymer matrix (e.g., PLGA) into a blood vessel can provide long-term treatment of, e.g., arterial disease in patients. The drug-eluting composite/material remains deployed within the host vessel after deflation and removal of the medical balloon. Drug is continuously provided in a time-released manner by the drug-eluting composite/material without need for a permanent medical device to be present in the body. The drug-eluting coating can continue to deliver a needed drug benefit over time.

Figure 7:
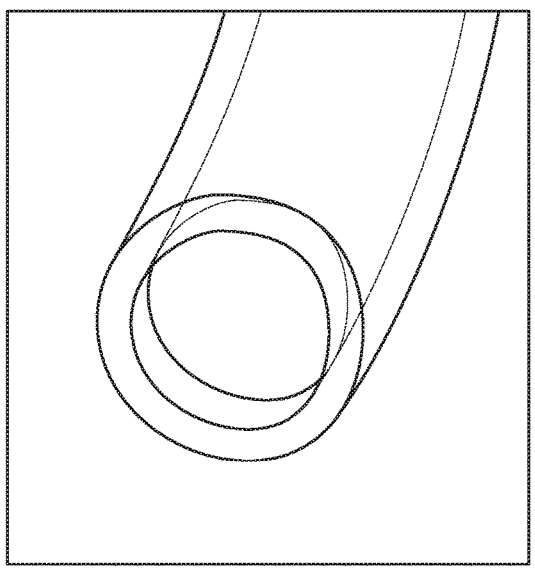
FIG. 7 shows a transferable, time-released drug-eluting coating delivered in accordance with an embodiment of the process of the invention.

FIG. 7 is a photomicrograph showing a polymer coating transferred from medical balloon onto the inner surface of medical-grade tubing (e.g., TYGON® medical tubing) that simulates transfer in an environment like those expected for delivery in mammalian hosts and human patients. The coating material was successfully transferred from the balloon surface to the inner wall (surface) of the medical tubing. The coating material on the surface of the medical balloon attaches to the host vessel upon expansion of the balloon. Removal and transfer of coating material from the balloon surface was effected in concert with a release layer composed of a low surface energy PTFE polymer (commercial-grade) that was deposited between the surface of the balloon and a first polymer layer prior to application of a subsequent PLGA polymer layer. So-called "release layers" are preferably, but not exclusively used. In the instant test, release was accomplished by inserting the coated balloon into TYGON® tubing, expanding the balloon at a temperature of 37° C., and pressing the expanded balloon on the inner wall of the tubing for about 2 minutes at equilibrium, or for 1 minute at a pressure of about 250 psi while immersing in an aqueous bath. Pressure used in this test is comparable to pressures used to deploy medical balloons in typical medical procedures. Results showed the entire polymer coating deposited on the balloon surface was transferred to the inner wall of the tube, forming the polymer coating. The outermost layer of the transferable coating material that becomes the innermost layer of the transferred composite deposited in the vessel lumen is preferably, but not exclusively, a coherent layer. The transferred material may further consist of partial or incomplete layers.

Effecting Net Charge of Transferred Material Surface

In other embodiments, release and transfer of the transferable coating material from the surface of the medical device to the vessel wall of the host or patient may be further enhanced by adding a net positive or net negative charge to the outermost surface of the transferable coating. This enhanced charge can also enhance attraction or otherwise promote adhesion of the coating particles to the surface of the vessel wall to which the coating is delivered. Such charge can also promote uptake of the therapeutic agent present within the transferred coating material into various cells of the patient or host where tissue damage induced by balloon expansion can be treated. The outermost coating layer on the surface of the medical balloon is preferably, but not exclusively, charged with a net positive charge. In some embodiments, a net positive charge enhances the attraction of the coating material on the surface of the expandable delivery device to the receiving surface of the host vessel. Although a positive net charge is described here, choice of charge is not limited. Tests on host vessel surrogates have demonstrated the ability to transfer polymer and drug coating materials at conditions similar to those found in a human body.

Provided herein is a method for forming an implantable, drug-eluting coating on the surface of an expandable medical device, characterized by the steps of: mounting an expandable delivery device with an internally disposed conducting member that maximizes conduction of charge on the surface of the device; delivering preselected potentials with the conducting member to the surface of the expandable delivery device to maximize collection of coating particles on the surface thereof; and coating the expandable delivery device with coating particles delivered via an e-RESS process, and e-STAT process, or a combined e-RESS process and e-STAT process to form one or more coating layers on the surface thereof.

In some embodiments, the expandable delivery device is a medical balloon. In some embodiments, at least one coating layer of the expandable delivery device includes a drug-eluting component and at least one coating layer includes a biosorbable polymer forming the implantable drug eluting coating on the surface of the device. In some embodiments, the medical balloon comprises nylon.

In some embodiments, the coating provides transfer of at least a portion of the one or more coating layers upon contact with a host vessel.

In some embodiments, wherein the expandable delivery device is at least a portion of a medical implant device. In some embodiments, the expandable delivery device is an interventional device. In some embodiments, the expandable delivery device is a diagnostic device. In some embodiments, the expandable delivery device is mounted to a delivery device prior to insertion into a host vessel. In some embodiments, the delivery device is a catheter.

In some embodiments, the conduction of charge on the surface is via gas-phase conduction or surface conduction of charge. In some embodiments, the delivering of preselected potentials includes delivering an active potential with the conducting component. In some embodiments, the delivering of preselected potentials does not include applying an active potential to the conducting component. In some embodiments, the delivering includes applying an electrostatic field potential on the surface of the expandable delivery device of at least about 15 kV prior to the coating step with the e-STAT process.

In some embodiments, the biosorbable polymer and drug eluting component are located within the same coating layer. In some embodiments, the coating includes coating the surface simultaneously with the e-RESS process and the e-STAT process to encapsulate a drug and a biosorbable polymer in a single layer of the drug-eluting coating.

In some embodiments, the drug-eluting component includes a drug dispersed within a biosorbable polymer disposed in a single coating layer. In some embodiments, the biosorbable polymer and drug-eluting component are located in different coating layers. In some embodiments, at least one coating layer includes a binding component comprising polylactoglycolic acid (PLGA).

In some embodiments, the expandable delivery device is at least partially expanded during coating of same.

In some embodiments, at least a portion of the biosorbable polymer has a preselected molecular weight that enhances transferability of the drug-eluting coating to the receiving surface within the host vessel. In some embodiments, the drug is a time-released drug that provides time-selectivity for treatment of a host or patient. In some embodiments, the drug has a crystalline form. In some embodiments, the drug comprises sirolimus.

In some embodiments, the coating includes masking one or more preselected portions of the expandable delivery device. In some embodiments, the masking includes forming preselected shapes selected from: oval, square, rectangle, triangular, or cylindrical within the coating layers on the surface of the expandable delivery device that contain an active drug delivered in the drug-eluting coating when in contact with the receiving surface.

In some embodiments, at least one coating layer includes a releasing agent selected from the group consisting of hydrophilic or hydrophobic chemicals or polymers that lower the interfacial energy between the surface of the medical device and the coating layers, water soluble chemicals or polymers that dissolve to eliminate adhesion between coatings layers and the medical device surface, brittle or friable coatings that lose mechanical cohesion upon, polyethylene glycols (PEG), hydrogels, polyesters, polyacrylates, polysaccharides, silicones, silanes, tocopherol, glycerin, sucrose, cellulose, shellac, and combinations thereof providing release of the coating to the receiving surface upon contact with same. In some embodiments, the releasing agent is located within a coating layer disposed between the surface of the expandable delivery device and a first layer comprising a biosorbable polymer.

In some embodiments, at least one coating layer on the surface of the expandable delivery device comprises a low-energy releasing agent selected from the group consisting of a releasing agent with surface energy of less than 35 dynes/cm or agents onto which a drop of water would experience a contact angle of greater than 90 degrees, polyvinyl alcohols (PVA), ethylene vinyl acetates (EVA), folyolefins, fluorosilanes, fluoroacrylates, fluorohydrocarbons, paraffin, long chain hydrocarbons, and combinations thereof. In some embodiments, the low-energy releasing agent is located within a coating layer disposed between the surface of the expandable delivery device and a first layer comprising a biosorbable polymer.

In some embodiments, at least one coating layer on the surface of the expandable delivery device comprises an adhesive agent selected from the group consisting of agents with cationic moieties that assist in cellular adhesion/uptake, shattering agents that penetrate tissue surface and promote adhesion through mechanical entanglement, viscous polymeric agents, and cationic polyamino acids such as polyarginine, polylysine, polyhistidine, and polyethyleneimine (PEI), 3,4-dihydroxy-L-phenylalanine (dopa), (as in active component in mussel adhesive), laminins, cationic surfactant molecules such as didodecyldimethylammonium bromide (DMAB), ethylhexadecyldimethylammonium bromide, dodecyltrimethyl ammonium bromide, tetradodecylammonium bromide, dimethylditetradecylammonium bromide, detrabutylammonium iodide, DEAE-dextran hydrochloride, and hexadimethrine bromide, and combinations thereof that affixes the transferable coating material to the receiving surface upon expansion of the expandable delivery device. In some embodiments, the transferable coating material includes an adhesion layer that enhances adhesion with the receiving surface. In some embodiments, the adhesive agent is included with the biosorbable polymer in a single coating layer on the surface of the expandable delivery device.

In some embodiments, at least one coating layer includes both the biosorbable polymer and a drug or therapeutic agent to provide timed-release delivery of the drug or therapeutic agent by dissolution of the biosorbable polymer layer within the coating material transferred to the host vessel. In some embodiments, the leading layer of the transferable coating on the surface of the expandable delivery device contains therapeutic drug particles modified with a surface charge prior.

In some embodiments, the coating particles are of a size between about 0.01 micrometers and about 10 micrometers.

In some embodiments, the step of sintering the transferable coating material to form a dense, thermally stable film on the surface of the expandable delivery device prior to delivery of same at a temperature in the range from about 25° C. to about 150° C.

In some embodiments, the sintering includes sintering the transferable coating material in the presence of a solvent gas to form a dense, thermally stable film on the surface of the expandable delivery device.

In some embodiments, the method further includes the step of transferring at least a portion of the coating from the expandable delivery device to a receiving surface of a host vessel to form a drug-eluting deposit therein. In some embodiments, the transferring includes expanding the expandable delivery device to transfer and implant at least a portion of the drug-eluting coating to the receiving surface of the host vessel. In some embodiments, the step of expanding includes expanding the expandable delivery device using a fluid that maintains rigidity and integrity of along the external surface of same. In some embodiments, the expanding includes at least partially deflating the expandable delivery device to reduce the physical dimensions of the expandable delivery device when inserting same into the host vessel prior to transferring the coating to the receiving surface of the host vessel.

Provided herein are devices comprising the elements noted herein, which may be produced according to methods described herein.

While exemplary embodiments of the present invention have been shown and described herein, it will be apparent to those skilled in the art that many changes and modifications may be made without departing from the invention in its true scope and broader aspects. The appended claims are therefore intended to cover all such changes and modifications as fall within the spirit and scope of the invention.

What is claimed is:

1. A method for forming an implantable, drug-eluting coating on the surface of an expandable medical device, characterized by the steps of:

mounting an expandable delivery device on each of a plurality of conducting members such that each conducting member is internally disposed within a different one of a plurality of expandable delivery device, the conducting members being oriented around a circle;

delivering preselected potentials with each conducting member to a surface of the expandable delivery devices in which the conducting member is disposed to optimize collection of coating particles on the surfaces of the expandable delivery device; and coating the expandable delivery devices with coating particles delivered via an e-RESS process, an e-STAT process, or a combined e-RESS process and e-STAT process to form one or more coating layers on the surfaces thereof, wherein the coating particles are concurrently delivered to the surfaces of each one of the plurality of delivery devices via an e-RESS coating nozzle, an E-STAT coating nozzle, or the e-RESS coating nozzle and the E-STAT coating nozzle.

2. The method of claim 1, wherein each expandable delivery device is a medical balloon.

3. The method of claim 1, wherein at least one coating layer of each expandable delivery device includes a drug-eluting component and at least one coating layer includes a biosorbable polymer forming the implantable drug eluting coating on the surfaces of the devices.

4. The method of claim 1, wherein the coating provides transfer of at least a portion of the one or more coating layers upon contact with a host vessel.

5. The method of claim 2, where the medical balloons comprise nylon.

6. The method of claim 1, wherein each expandable delivery device is at least a portion of a medical implant device.

7. The method of claim 1, wherein each expandable delivery device is an interventional device.

8. The method of claim 1, wherein each expandable delivery device is a diagnostic device.

9. The method of claim 1, wherein each expandable delivery device is mounted to a delivery device prior to insertion into a host vessel.

10. The method of claim 9, wherein each delivery device is a catheter.

11. The method of claim 1, wherein a conduction of charge on the surface is via gas-phase conduction or surface conduction of charge.

12. The method of claim 1, wherein the delivering includes applying an electrostatic field potential on the surfaces of each expandable delivery device of at least about 15 kV prior to the coating step with the e-STAT process.

13. The method of claim 3, wherein the biosorbable polymer and drug eluting component are located within the same coating layer.

14. The method of claim 3, wherein the coating includes coating the surfaces simultaneously with the e-RESS process and the e-STAT process to encapsulate a drug and a biosorbable polymer in a single layer of the drug-eluting coating.

15. The method of claim 3, wherein the drug-eluting component includes a drug dispersed within a biosorbable polymer disposed in a single coating layer.

16. The method of claim 3, wherein the biosorbable polymer and drug-eluting component are located in different coating layers.

17. The method of claim 1, wherein at least one coating layer includes a binding component comprising polylactoglycolic acid (PLGA).

18. The method of claim 1, wherein each expandable delivery device is at least partially expanded during coating of same.

19. The method of claim 3, wherein at least a portion of the biosorbable polymer has a preselected molecular weight that enhances transferability of the drug-eluting coating to a receiving surface within a host vessel.

20. The method of claim 19, wherein the drug is a time-released drug that provides time-selectivity for treatment of a host or patient.

21. The method of claim 19, wherein the drug has a crystalline form.

22. The method of claim 19, wherein the drug comprises sirolimus.

23. The method of claim 1, wherein the coating includes masking one or more preselected portions of each expandable delivery device.

24. The method of claim 23, wherein the masking includes forming preselected shapes selected from: oval, square, rectangle, triangular, or cylindrical within the coating layers on the surfaces of the expandable delivery devices that contain an active drug delivered in the drug-eluting coating when in contact with a receiving surface.

25. The method of claim 1, wherein at least one coating layer includes a releasing agent selected from the group consisting of: hydrophilic or hydrophobic chemicals or polymers that lower the interfacial energy between the surface of the medical device and the coating layers, water soluble chemicals or polymers that dissolve to eliminate adhesion between coatings layers and the medical device surface, brittle or friable coatings that lose mechanical cohesion upon, polyethylene glycols (PEG), hydrogels, polyesters, polyacrylates, polysaccharides, silicones, silanes, tocopherol, glycerin, sucrose, cellulose, shellac, and combinations thereof providing release of the coating to the receiving surface upon contact with same.

26. The method of claim 25, wherein the releasing agent is located within a coating layer disposed between the surface of the expandable delivery device and a first layer comprising a biosorbable polymer.

27. The method of claim 1, wherein at least one coating layer on the surface of the expandable delivery device comprises a low-energy releasing agent selected from the group consisting of: a releasing agent with surface energy of less than 35 dynes/cm or agents onto which a drop of water would experience a contact angle of greater than 90 degrees, polyvinyl alcohols (PVA), ethylene vinyl acetates (EVA), folyolefins, fluorosilanes, fluoroacrylates, fluorohydrocarbons, paraffin, long chain hydrocarbons, and combinations thereof.

28. The method of claim 27, wherein the low-energy releasing agent is located within a coating layer disposed between the surface of the expandable delivery device and a first layer comprising a biosorbable polymer.

29. The method of claim 1, wherein at least one coating layer on the surface of the expandable delivery device comprises an adhesive agent selected from the group consisting of: agents with cationic moieties that assist in cellular adhesion/uptake, shattering agents that penetrate tissue surface and promote adhesion through mechanical entanglement, viscous polymeric agents, and cationic polyamino acids such as polyarginine, polylysine, polyhistidine, and polyethyleneimine (PEI), 3,4-dihydroxy-L-phenylalanine (dopa), (as in active component in mussel adhesive), laminins, cationic surfactant molecules such as didodecyldimethylammonium bromide (DMAB), ethylhexadecyldimethylammonium bromide, dodecyltrimethyl ammonium bromide, tetradodecylammonium bromide, dimethylditetradecylammonium bromide, detrabutylammonium iodide, DEAE-dextran hydrochloride, and hexadimethrine bromide, and combinations thereof that affixes the coating to a receiving surface upon expansion of the expandable delivery device.

30. The method of claim 29, wherein the adhesive agent enhances adhesion with the receiving surface.

31. The method of claim 29, wherein the adhesive agent is included with a biosorbable polymer in a single coating layer on the surface of the expandable delivery device.

32. The method of claim 1, wherein at least one coating layer includes both a biosorbable polymer and either a drug or a therapeutic agent to provide timed-release delivery of the drug or the therapeutic agent by dissolution of the biosorbable polymer layer.

33. The method of claim 1, wherein at least one coating layer of the coating on the surface of the expandable delivery device contains therapeutic drug particles modified with a surface charge prior.

34. The method of claim 1, wherein the coating particles are of a size between about 0.01 micrometers and about 10 micrometers.

35. The method of claim 1, further including the step of sintering the coating to form a dense, thermally stable film on the surfaces of each expandable delivery device prior to delivery of same at a temperature in the range from about 25° C. to about 150° C.

36. The method of claim 35, wherein the sintering includes sintering the coating in the presence of a solvent gas to form a dense, thermally stable film on the surfaces of each expandable delivery device.

37. The method of claim 1, further including a step of transferring at least a portion of the coating from at least one of the expandable delivery devices to a receiving surface of a host vessel to form a drug-eluting deposit therein.

38. The method of claim 37, wherein the transferring step includes expanding the expandable delivery device to transfer and implant at least a portion of the drug-eluting coating to the receiving surface of the host vessel.

39. The method of claim 38, wherein the step of expanding includes expanding the expandable delivery device using a fluid that maintains rigidity and integrity along an external surface of the delivery device.

40. The method of claim 38, wherein the expanding includes at least partially deflating the expandable delivery device to reduce the physical dimensions of the expandable delivery device when inserting the delivery device into the host vessel prior to transferring the coating to the receiving surface of the host vessel.

41. The method of claim 1, wherein each of the internally disposed conducting members are located on a ring and extend along a longitudinal axis of a respective expandable delivery device and substantially an entire length of the respective expandable delivery devices.

42. The method of claim 41, wherein the mounting step includes contacting each of the plurality of expandable delivery devices with the ring.

43. The method of claim 42, wherein the ring includes upper and lower rings, the plurality of expandable delivery devices being in contact with the upper ring.

* * * * *